(12) United States Patent
Ambati

(10) Patent No.: US 7,553,496 B2
(45) Date of Patent: Jun. 30, 2009

(54) VEGF-A AS AN INHIBITOR OF ANGIOGENESIS AND METHODS OF USING SAME

(75) Inventor: Jayakrishna Ambati, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 247 days.

(21) Appl. No.: 11/017,201

(22) Filed: Dec. 21, 2004

(65) Prior Publication Data

US 2006/0135423 A1    Jun. 22, 2006

(51) Int. Cl.
*A61F 2/00* (2006.01)
*A61K 39/395* (2006.01)
*A61K 38/18* (2006.01)
*A61K 31/70* (2006.01)

(52) U.S. Cl. .................. 424/427; 514/12; 514/44; 424/130.1

(58) Field of Classification Search .................. None
See application file for complete search history.

(56) References Cited

U.S. PATENT DOCUMENTS

| | | | |
|---|---|---|---|
| 6,177,401 B1 | 1/2001 | Ullrich et al. | |
| 6,397,849 B1 * | 6/2002 | Bowman et al. | 128/898 |
| 6,524,799 B1 * | 2/2003 | Walker et al. | 435/6 |
| 7,335,371 B2 * | 2/2008 | Sackeyfio et al. | 424/400 |
| 2002/0151680 A1 | 10/2002 | Alitalo et al. | |
| 2003/0118579 A1 * | 6/2003 | Walker et al. | 424/94.63 |
| 2004/0110757 A1 * | 6/2004 | Arrhenius et al. | 514/241 |
| 2005/0176669 A1 * | 8/2005 | Al-Murrani | 514/44 |

OTHER PUBLICATIONS

Kupprion et al., Journal of Biological Chemistry, 273(45):29635-29640, 1998.*
Shih, S. et al., *Selective stimulation of VEGER-1 prevents oxygen-induced retinal vascular degeneration in retinopathy of prematurity.* (2003) J Clinical Invest 112, 50-57.
Carmeliet, P. et al. *Synergism between vascular endothelial growth factor and placental growth factor contributes to angiogenesis and plasma extravasation in pathological conditions.* (2001) Nat Med 7, 575-83.
Hiratsuka, S. et al. *Involvement of flt-1 tyrosine kinase (vascular endothelial growth factor receptor-1) in pathological angiogenesis.* (2001) Cancer Res 61, 1207-1213.
Bussolati, B. et al. *Vascular endothelial growth factor receptor-1 modulates vascular endothelial growth factor-mediated angiogenesis via nitric oxide.* (2001) Am J Pathol 159, 993-1008.
Lopez, P. F., et al., *Transdifferentiated retinal pigment epithelial cells are immunoreactive for vascular endothelial growth factor in surgically excised age-related macular degeneration-related choroidal neovascular membranes.* (1996) Invest Ophthalmol Vis Sci 37, 855-68.
Saishin, Y. et al. *VEGF-TRAPR1R2 suppresses choroidal neovascularization and VEGF-induced breakdown of the blood-retinal barrier.* (2003) J Cell Physiol 195, 241-8. These data are the bases for current clinical trials of anti-VEGF-A therapy in patients with AMD.
Spilsbury, K., et al., *Overexpression of vascular endothelial growth factor (VEGF) in the retinal pigment epithelium leads to the development of choroidal neovascularization.* (2000) Am J Pathol 157, 135-44.
Schwesinger, C. et al. *Intrachoroidal neovascularization in transgenic mice overexpressing vascular endothelial growth factor in the retinal pigment epithelium.* (2001) Am J Pathol 158, 1161-1172.
Oshima, Y. et al. *Increased expression of VEGF in retinal pigmented epithelial cells is not sufficient to cause choroidal neovascularization.* J Cell Physiol Published Online: Jun. 7, 2004, DOI: 10.1002/jcp.20110 (2004).
Schmidt-Erfurth, U. et al. *Influence of photodynamic therapy on expression of vascular endothelial growth factor (VEGF), VEGF receptor 3, and pigment epithelium-derived factor.* (2003) Invest. Ophthalmol. Vis. Sci. 44, 4473-4480.
Grossniklaus, H. E. et al. Macrophage and retinal pigment epithelium expression of angiogenic cytokines in choroidal neovascularization. (2002) *Mol Vis* 8, 119-26.
Sakurai, E. et al. *Targeted disruption of the CD18 or ICAM-1 gene inhibits choroidal neovascularization.* (2003) Invest Ophthalmol Vis Sci 44, 2743-9.
Sakurai, E., et al., *Macrophage depletion inhibits experimental choroidal neovascularization.* (2003) Invest Ophthalmol Vis Sci 44, 3578-85.

* cited by examiner

*Primary Examiner*—Marianne P Allen
(74) *Attorney, Agent, or Firm*—McDermott Will & Emery LLP

(57) ABSTRACT

The invention relates to methods and compositions for the treatment or prevention of ocular angiogenesis and neovascularization associated with neovascular disease. Administration of vascular endothelial growth factor (VEGF)-A into the eye when macrophage infiltration is reduced inhibits ocular angiogenesis.

4 Claims, 20 Drawing Sheets

VEGF-A AS AN INHIBITOR OF ANGIOGENESIS AND METHODS OF USING SAME

FIELD OF THE INVENTION

The present invention relates to the use of VEGF-A to inhibit angiogenesis, cell proliferation and inflammation. The present invention relates to the use of VEGF-A, PLGF-1, PLGF-2 or combinations thereof to treat and/or prevent ocular neovascularization, angiogenesis, cell proliferation and inflammation associated with neovascular disease and/or traumatic ocular injury. The present invention also relates to proteins, peptides, organic molecules and reagents capable of modulating VEGF-A/VEGFR-1 interaction to effect activation or inhibition of ocular neovascularization.

BACKGROUND OF THE INVENTION

Vascular endothelial growth factor A (VEGF-A), which signals through the receptor tyrosine kinases VEGFR-1 and VEGFR-2, plays a dominant role in physiologic and pathologic angiogenesis, with VEGFR-2 implicated as its principal pro-angiogenic transducer. The function of VEGFR-1 is more nebulous. Although deletion of the vegfr-1 gene results in embryonic lethality due to endothelial overcrowding (Fong, G., Zhang, L., Bryce, D. & Peng, J. *Increased hemangioblast commitment, not vascular disorganization, is the primary defect in flt-1 knock-out mice*. (1999) Development 126, 3015-3025), vascular development is grossly unscathed in mice with a deletion of its kinase domain (vegfr-1 tk$^{-/-}$) (Hiratsuka, S., Minowa, O., Kuno, J., Noda, T. & Shibuya, M. *Flt-1 lacking the tyrosine kinase domain is sufficient for normal development and angiogenesis in mice*. (1998) Proc Natl Acad Sci USA 95, 9349-54), suggesting that VEGFR-1 subserves a negative role in embryogenesis by acting as a scavenger/decoy. However, conflicting data about VEGFR-1 function has emerged from studies that demonstrate that it both amplifies (Carmeliet, P. et al. *Synergism between vascular endothelial growth factor and placental growth factor contributes to angiogenesis and plasma extravasation in pathological conditions*. (2001) Nat Med 7, 575-83; Hiratsuka, S. et al. *Involvement of flt-1 tyrosine kinase (vascular endothelial growth factor receptor-1) in pathological angiogenesis*. (2001) Cancer Res 61, 1207-1213) and antagonizes (Bussolati, B. et al. *Vascular endothelial growth factor receptor-1 modulates vascular endothelial growth factor-mediated angiogenesis via nitric oxide*. (2001) Am J Pathol 159, 993-1008) pathologic angiogenesis. Thus VEGFR-1 signaling appears to be highly cell/tissue-specific and context/stage-dependent.

Choroidal neovascularization (CNV) is the principal cause of blindness in patients with age-related macular degeneration (AMD), which is responsible for vision loss in 25-30 million people worldwide. Smith, W. et al. *Risk factors for age-related macular degeneration: Pooled findings from three continents*. (2001) Ophthalmology 108, 697-704. VEGF-A is present in CNV membranes surgically excised from patients with AMD (Lopez, P. F., Sippy, B. D., Lambert, H. M., Thach, A. B. & Hinton, D. R. *Transdifferentiated retinal pigment epithelial cells are immunoreactive for vascular endothelial growth factor in surgically excised age-related macular degeneration-related choroidal neovascular membranes*. (1996) Invest Ophthalmol Vis Sci 37, 855-68), and pharmacological inhibition of VEGF-A decreases experimental laser-induced CNV. Saishin, Y. et al. *VEGF-TRAP$_{R1R2}$ suppresses choroidal neovascularization and VEGF-induced breakdown of the blood-retinal barrier*. (2003) J Cell Physiol 195, 241-8. These data are the bases for current clinical trials of anti-VEGF-A therapy in patients with AMD.

However, the precise role of VEGF-A in CNV still is unclear. While subretinal injection of viral vectors coding for VEGF-A leads to retinal pigmented epithelium (RPE) overexpression of VEGF-A and subsequent CNV (Spilsbury, K., Garrett, K. L., Shen, W. Y., Constable, I. J. & Rakoczy, P. E. *Overexpression of vascular endothelial growth factor (VEGF) in the retinal pigment epithelium leads to the development of choroidal neovascularization*. (2000) Am J Pathol 157, 135-44), transgenic VEGF-A upregulation directed by RPE-specific promoters such as RPE65 or VMD2 does not produce CNV. Schwesinger, C. et al. *Intrachoroidal neovascularization in transgenic mice overexpressing vascular endothelial growth factor in the retinal pigment epithelium*. (2001) Am J Pathol 158, 1161-1172. Oshima, Y. et al. *Increased expression of VEGF in retinal pigmented epithelial cells is not sufficient to cause choroidal neovascularization*. J Cell Physiol Published Online: 7 Jun. 2004, DOI: 10.1002/jcp.20110 (2004). However, transgenic VEGF-A upregulation coupled with subretinal injection of null viral vector induced CNV (Oshima, Y. et al. 2004), suggesting that increased VEGF-A alone is insufficient to induce CNV without coexisting mechanical trauma or immune deviation. In addition, the results of a large clinical trial of an anti-VEGF-A aptamer in CNV have yielded mixed results (http://www.fda.gov/ohrms/dockets/ac/04/briefing/2004-4053B1_02_FDA-Backgrounder.pdf).

This trial demonstrated an inverse dose response, with the highest dose of Macugen® (Eyetech Pharmaceuticals, Inc.) showing no significant treatment effect. Although the lowest dose decreased the rate of vision loss over 1 year, it did not alter the inexorable increase in CNV lesion size. In addition, because a large fraction of patients treated with Macugen® also received photodynamic therapy with verteprofin (Visudyne®, QLT, Inc. and Novartis Opthalmics), a currently approved and widely used treatment, it is difficult to extract the effect of Macugen®. Paradoxically Visudyne® reduces the rate of increase in CNV lesion size despite increasing VEGF-A expression in the choroid. Schmidt-Erfurth, U. et al. *Influence of photodynamic therapy on expression of vascular endothelial growth factor (VEGF), VEGF receptor 3, and pigment epithelium-derived factor*. (2003) Invest. Ophthalmol. Vis. Sci. 44, 4473-4480.

While the role of VEGF-A in CNV is still unresolved, recruitment of macrophages, which is spatiotemporally correlated with arborizing CNV in patients with AMD, is known to be operative in the development of CNV. Grossniklaus, H. E. et al. *Macrophage and retinal pigment epithelium expression of angiogenic cytokines in choroidal neovascularization*. (2002) Mol Vis 8, 119-26. Sakurai, E. et al. *Targeted disruption of the CD18 or ICAM-1 gene inhibits choroidal neovascularization*. (2003) Invest Ophthalmol Vis Sci 44, 2743-9. Sakurai, E., Anand, A., Ambati, B. K., van Rooijen, N. & Ambati, J. *Macrophage depletion inhibits experimental choroidal neovascularization*. (2003) Invest Ophthalmol Vis Sci 44, 3578-85. Because VEGF-A is a chemoattractant for monocyte-derived cells, there is a need for understanding the interactions between VEGF-A and macrophages in CNV, and the roles of VEGFR-1 and VEGFR-2 in this process.

Tight regulation of VEGF-A following injury permits coordinated orchestration of angiogenesis and inflammation, initiated by arrival of inflammatory cells followed by endothelial proliferation. The transient decline in SPARC immediately following injury temporarily unsilences VEGFR-1 tyrosine kinase activity, promoting VEGF-A signaling via VEGFR-1. Increasing VEGF-A levels during this period not only disrupts leukocyte recruitment by inducing anti-inflammatory pathways via excess VEGFR-1 stimulation, but also arrests endothelial cells, disadvantaging their proliferation in the angiogenesis stage. This Janus-like effect reveals novel therapeutic strategies to modulate angiogenesis in the setting of inflammation and highlights the importance of developing the ability to assay expression of markers such as SPARC to target therapeutics more specifically.

SUMMARY OF THE INVENTION

The present invention pertains to mammalian vascular endothelial growth factors which interact with vascular endothelial growth factor receptor 1 (VEGFR-1) and VEGFR-2 to modulate angiogenesis. Several different growth factors which interact with VEGFR-1 were identified to inhibit angiogenesis after traumatic ocular injury. The present invention provides the use of endogenous and exogenous VEGF-A, PLGF-1, PLGF-2 and combinations thereof to inhibit and treat pathologic ocular angiogenesis, ocular neovascularization, cell proliferation and inflammation associated with neovascular disease and/or traumatic ocular injury.

In one aspect of the invention there is provided a method for inhibiting angiogenesis in the eye of a subject in need thereof comprising administering to the subject a therapeutically effective amount of VEGF-A, PLGF-1, PLGF-2 or a combination thereof after ocular injury but prior to macrophage recruitment. In a preferred embodiment, VEGF-A, PLGF-1, PLGF-2 or combinations thereof are administered topically or via direct injection into the eye. In another aspect is the use of VEGF-A, PLGF-1, PLGF-2 or a combination thereof to inhibit angiogenesis.

In yet another aspect of the invention there is provided a composition for application to an eye of a subject in need of treatment or prevention of angiogenesis in the eye comprising VEGF-A, PLGF-1, PLGF-2 or a combination thereof, and a pharmaceutically acceptable carrier.

There is also provided a method for treating or preventing ocular neovascularization in a subject in need thereof comprising administering to the subject a therapeutically effective amount of VEGF-A, PLGF-1, PLGF-2 or a combination thereof after ocular injury but prior to macrophage recruitment. In different embodiments, ocular neovascularization is choroidal neovascularization, corneal neovascularization, iris neovascularization, retinal pigmented epithelium (RPE) neovascularization, vitreal neovascularization, neovascularization associated with age-related macular degeneration (AMD), and neovascularization associated with retinopathy of prematurity. In a preferred embodiment, VEGF-A, PLGF-1, PLGF-2 or combinations thereof are administered topically or via direct injection into the eye. In another aspect, is the use of VEGF-A, PLGF-1, PLGF-2 or a combination thereof to treat or prevent ocular neovascularization.

In yet another aspect of the invention there is provided a composition for application to an eye of a subject in need of treatment or prevention of ocular neovascularization comprising VEGF-A, PLGF-1, PLGF-2 or a combination thereof and a pharmaceutically acceptable carrier.

The present invention is also based on the discovery that the in vivo anti-angiogenic effects of VEGF-A, PLGF-1 and PLGF-2 are mediated through the VEGF receptor (VEGFR)-1. Several pathways affect whether VEGF-A, PLGF_1 and PLGF-2 are mediated through VEGFR-1 or VEGF receptor (VEGFR)-2. VEGFR-2 signaling is inhibited, thus promoting VEGFR-1 signaling, via induction of phosphatase SHP-1 that binds to and deactivates VEGFR-2. VEGFR-2 signaling is inhibited, thus promoting VEGFR-1 signaling, which induces heme oxygenase (HO)-1 that inhibits the downstream consequences of VEGFR-2 signaling. At rest, VEGFR-1 activation is silenced by secreted protein, acidic, rich in cysteine (SPARC), which declines transiently after injury, thereby creating a temporal window where VEGF-A, PLGF-1 and PLGF-2 signaling is routed principally through VEGFR-1.

In a further aspect, the invention provides a method of inhibiting angiogenesis in an eye of a subject in need thereof comprising inducing VEGFR-1 activity. In one embodiment, the VEGFR-1 activity is induced by antagonizing SPARC. Methods of antagonizing SPARC include administration of compounds that interact with SPARC so as to unsilence the activity of VEGFR-1. Preferably the compound is an antagonist of SPARC. In a preferred embodiment, the compound is an antibody to SPARC. In another embodiment, the method further comprises administering to the eye, substantially together with a SPARC antagonist, VEGF-A, PLGF-1, PLGF-2 or a combination thereof, and a pharmaceutically acceptable carrier.

In a further aspect of the invention is provided a method for treating or preventing ocular neovascularization comprising administering to the eye of a subject in need thereof a therapeutically effective amount of a SPARC antagonist and pharmaceutically acceptable carrier. In one embodiment the method further comprises administering substantially together with the SPARC antagonist, VEGF-A, PLGF-1, PLGF-2 or a combination thereof. In different embodiments, ocular neovascularization is choroidal neovascularization, corneal neovascularization, iris neovascularization, retinal pigmented epithelium (RPE) neovascularization, vitreal neovascularization, neovascularization associated with age-related macular degeneration (AMD), and neovascularization associated with retinopathy of prematurity. In a preferred embodiment, VEGF-A, PLGF-1, PLGF-2 or combinations thereof are administered topically or via direct injection into the eye.

In a preferred embodiment, there is a method of treating or preventing ocular neovascularization in a subject with reduced SPARC expression comprising administering to the subject a therapeutically effective amount of a composition comprising VEGF-A, PLGF-1, PLGF-2 or a combination thereof, and a pharmaceutically acceptable carrier.

In another aspect of the invention is provided a composition for treating or preventing ocular neovascularization comprising a SPARC antagonist and a pharmaceutically acceptable carrier. In one embodiment, the composition further comprises VEGF-A, PLGF-1, PLGF-2 or a combination thereof.

In another aspect of the invention there is a method of identifying a modulator of SPARC interacting with VEGFR-1 comprising the steps of: (a) measuring interaction between SPARC and VEGFR-1 in the presence and absence of a test compound under conditions that allow SPARC to silence VEGFR-1, and (b) identifying as a modulator a test compound which alters SPARC silencing of VEGFR-1. Preferably, the compound is an antagonist of SPARC or any substance interfering with SPARC interaction with VEGF-A or VEGFR-1.

In yet another aspect of the invention there is provided a method for determining a course of treatment for ocular neovascularization comprises measuring the amount of SPARC in an eye of a subject in need thereof, comprising: (1) introducing into the vitreous of an eye an antibody conjugated to a fluorescent label that binds to SPARC, (2) measuring the amount of fluorescence in the eye, and (3) determining the course of treatment based on the results, wherein a low or reduced level of SPARC, relative to a normal individual, is indicative that VEGF-A, PLGF-1 and/or PLGF-2 would be principally routed through VEGFR-1, and a high or increased level of SPARC, relative to a normal individual, is indicative that VEGF-A, PLGF-1 and/or PLGF-2 would be principally routed through VEGFR-2 signaling. In another embodiment, the method for measuring the amount of SPARC comprises: (1) taking a sample of vitreous or subretinal fluid from an eye of a subject in need thereof, (2) introducing into the sample an antibody conjugated to a fluorescent label that binds to SPARC, and (3) measuring the amount of fluorescence in the sample. In another embodiment, the method to assess SPARC levels in the choroid/RPE comprises injecting a SPARC antibody or other small molecule (e.g., aptamer) that binds to SPARC, coupled with a fluorescent reporter dye, and then imaging the eye for this fluorescent signal by angiography. These methods for determining a course of treatment are not limited to the eye, but may be applied to other tissues which would benefit from optimizing VEGF-A/VEGFR-1 interaction.

In another aspect of the invention there is a method of determining a dosage amount of an anti-VEGF-A therapy for a subject in need thereof, comprising measuring intraocular, subretinal and/or choroidal levels of SPARC and VEGF-A, wherein low levels of SPARC and high levels of VEGF-A, relative to a normal individual, are indicative that the dosage amount of anti-VEGF drugs should be decreased, and wherein, high levels of SPARC and low to moderate levels of VEGF-A, relative to a normal individual, are indicative that the dosage amount of anti-VEGF drugs should be increased.

In yet another aspect of the invention, there is a method of inhibiting angiogenesis by antagonizing VEGFR-2 activity to induce VEGFR-1 cell signaling mediated by VEGF-A, PLGF-1 and/or PLGF-2 signaling via VEGFR-1. In one embodiment, VEGFR-2 activity is antagonized by protein tyrosine phosphatase (PTP) Src homology domain 2 (SH2)-containing tyrosine phosphatase-1 (SHP-1) binding to VEGFR-2. VEGFR-2 kinase is antagonized by activation of SHP-1.

In still another embodiment, VEGFR-2 activity is antagonized by heme oxygenase (HO)-1 activity. VEGFR-2 signaling and downstream proliferative signals are antagonized by activation of heme oxygenase (HO)-1. HO-1 interferes with and/or inhibits the upregulation of Ccl-2, a consequence of VEGFR-2 interaction with VEGF-A.

In further aspect of the invention there is a method of treating or preventing ocular neovascularization comprising administering to the eye of a subject in need thereof a SHP-1 agonist, or a HO-1 agonist, or a combination thereof, and a pharmaceutically acceptable carrier. In one embodiment, the method further comprises administering to the eye, substantially together with a SHP-1 and/or HO-1 agonist, VEGF-A, PLGF-1, PLGF-2 or a combination thereof. In a preferred embodiment, there is a method of treating or preventing ocular neovascularization in a subject with increased SHP-1 and/or HO-1 expression comprising administering to the subject a therapeutically effective amount of a composition comprising VEGF-A, PLGF-1, PLGF-2 or a combination thereof and a pharmaceutically acceptable carrier.

In another aspect of the invention is provided a composition for treating or preventing ocular neovascularization comprising a SHP-1 and/or HO-1 agonist and a pharmaceutically acceptable carrier. In a preferred embodiment, the composition further comprises VEGF-A, PLGF-1, PLGF-2 or a combination thereof.

In another aspect of the invention is provided a method for identifying a modulator of SHP-1 inactivation of VEGFR-2 comprising the steps of: (a) measuring interaction between VEGFR-2 and SHP-1 in the presence and absence of a test compound under conditions that allow activation of SHP-1 to inhibit and/or deactivate VEGFR-2, and (b) identifying as a modulator a test compound which alters VEGFR-2 interaction with SHP-1. Preferably, the test compound is an agonist of SHP-1.

In another aspect of the invention is provided a method for identifying a modulator of HO-1 inactivation of Ccl-2/MCP-1 to reduce macrophage infiltration comprising the steps of: (a) measuring interaction between Ccl-2 and HO-1 in the presence and absence of a test compound under conditions that allow activation of HO-1 to inhibit and/or deactivate Ccl-2, and (b) identifying as a modulator a test compound which alters Ccl-2 interaction with HO-1. Preferably, the test compound is an agonist of HO-1.

In a further aspect of the invention there is a method of treating or preventing ocular neovascularization comprising administering to the eye of a subject in need thereof a therapeutically effective amount of a Ccl-2 antagonist and/or Ccr-2 antagonist that inhibits Ccl-2 interaction with Ccr-2, substantially together with VEGF-A, PLGF-1, PLGF-2 or a combination thereof and a pharmaceutically acceptable carrier. In a preferred embodiment, there is a method of treating or preventing ocular neovascularization in a subject with increased Ccl-2 and/or Ccr-2 expression comprising administering to the subject a therapeutically effective amount of a composition comprising VEGF-A, PLGF-1, PLGF-2 or a combination thereof and a pharmaceutically acceptable carrier.

In still a further aspect of the invention there is a method of treating or preventing vasculogenesis comprising modulating stem cell incorporation into an area of neovascularization by promoting VEGF-A induced suppressed Ccl-2 activity.

In yet another further aspect of the invention, VEGF-A selectively inhibits hemangiogenesis (blood vessels) as opposed to lymphangiogenesis (lymphatic vessels).

All publications, patents and patent applications cited herein, whether supra or infra, are hereby incorporated by reference in their entirety.

BRIEF DESCRIPTION OF THE DRAWINGS

FIG. 1$d$ shows stacked confocal image of representative laser-induced CNV lesion in PBS treated eye is much larger than in VEGF-A (12 ng) or PlGF-1 (1250 ng) treated eyes, and comparable to VEGF-E (12 ng) treated eye. n=9-18. Scale bar 100 μm.

FIG. 1(i-j) illustrate VEGF-$A_{164}$ reduction in laser-induced CNV volume. (i) VEGF-$A_{164}$ (4 ng) (white bars) reduces laser-induced CNV volume at 1 and 2 weeks after laser injury, compared to PBS (black bars). *P<0.05 compared with PBS. n=12. (j) VEGF-$A_{164}$ (4 ng) (black bars) reduces laser-induced CNV volume at 1 week after laser injury, compared to PBS (white bar) when injected on days 0 or 1 after injury, and increases it if injected one day before injury. *P<0.05 compared with PBS. n=9-12.

shows (i) VEGFR-2 dephosphorylation inhibition of angiogenesis, because bis(maltolato)oxovanadium(IV) (BMOV), a pan-PTP inhibitor, abrogated VEGF-A-induced inhibition of CNV; (ii) VEGF-A-induced inhibition of CNV was abolished by sodium stibogluconate, a potent SHP-1 inhibitor, but not by calpeptin, a specific inhibitor of the closely related SHP-2; and (iii) demonstrates that Shp1$^{-/-}$ mice were resistant to VEGF-A-induced CNV suppression.

Figure 2A:
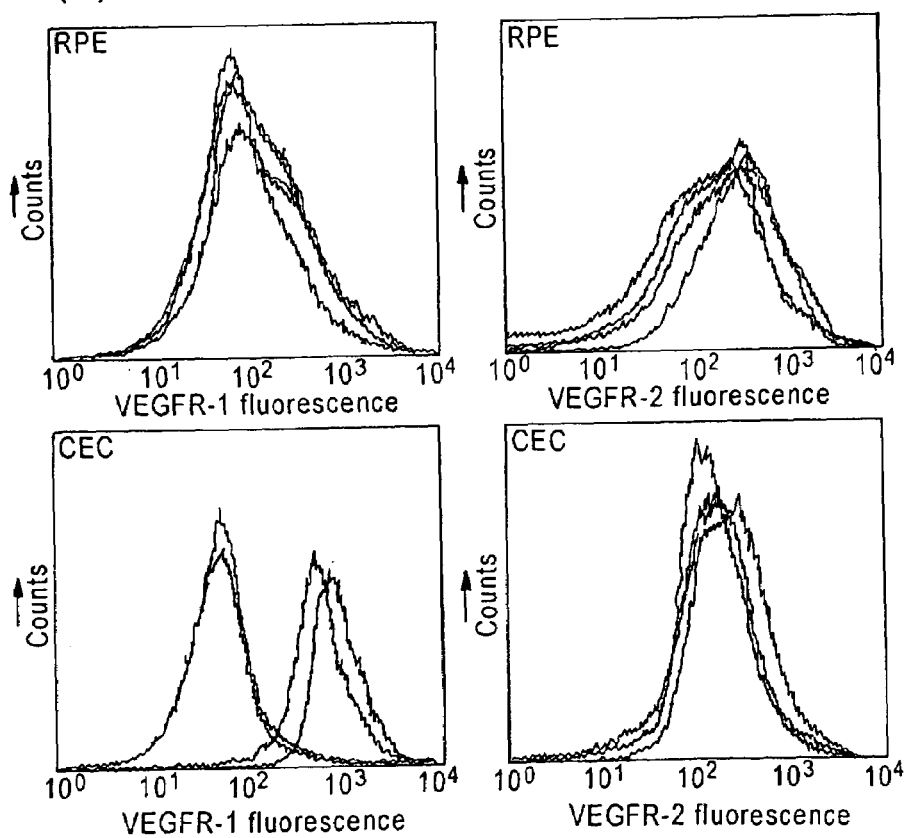
FIG. 2(a-e) shows that VEGF-A decreases CNV through VEGFR-1 induced negative transduction of VEGFR-2 via SHP-1. (a) Representative figures show that constitutive (black) VEGFR-1 and VEGFR-2 receptor number on CEC and RPE cells and on day 2 after laser injury (green), and on day 5 after injury for VEGF-A injected (red) and PBS-injected (blue) eyes. n=4-6. CEC expression of VEGFR-2 declines following laser injury (b) Cell surface RPE expression of VEGFR-1 (green) and VEGFR-2 (orange) is not changed by laser injury. CEC expression of VEGFR-1 (brown), but not VEGFR-2 (blue) decreases significantly following laser injury. Receptor expression levels are not significantly different between VEGF-A (dotted lines) and PBS (solid lines). n=4-6. #P<0.05, *P<0.01 compared with day 0 (before laser injury). (c) Representative figures show that VEGFR-1 and VEGFR-2 phosphorylation levels in RPE/choroid of eyes 30 min after intravitreous injection of PBS, VEGF-A, PlGF-1, or VEGF-E one day after injury. Western blotting for VEGFR-1 shows slightly higher expression in PBS-treated eyes. n=3. (d) Representative figures shows that VEGF-A, injected one day after laser injury, increases interaction of SHP-1 with VEGFR-2 and reduces VEGFR-2 phosphorylation at 30 min and 48 h after injection, without affecting VEGFR-2 expression. Densitometric ratios of SHP-1 to total VEGFR-2 and of phosphorylated (P) to total (T) VEGFR-1 are shown. n=4. (e)
Figure 2B:
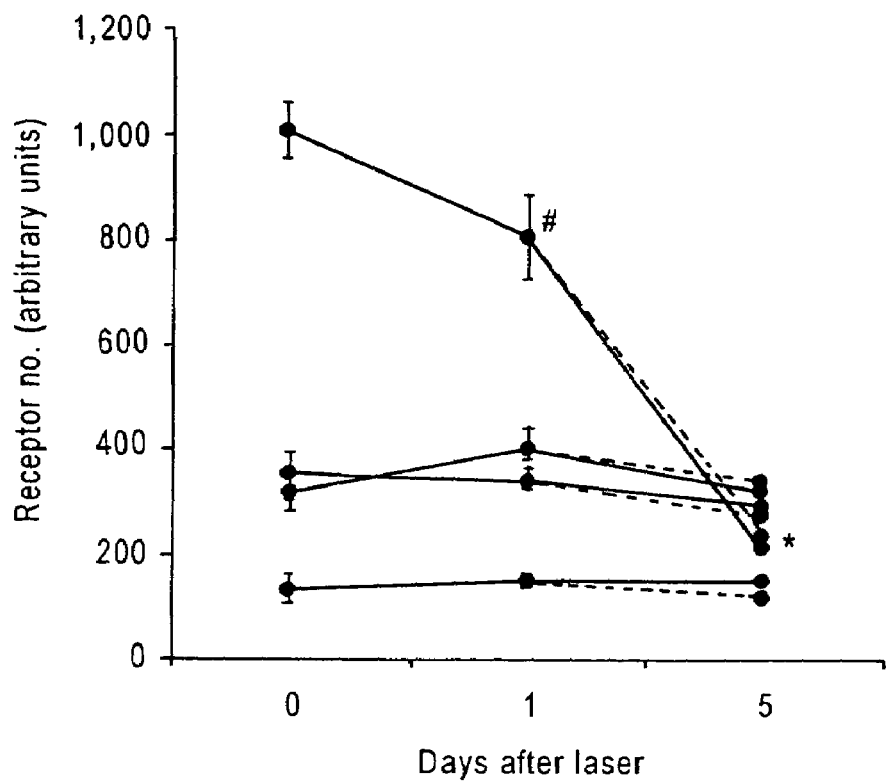
Figure 2C:
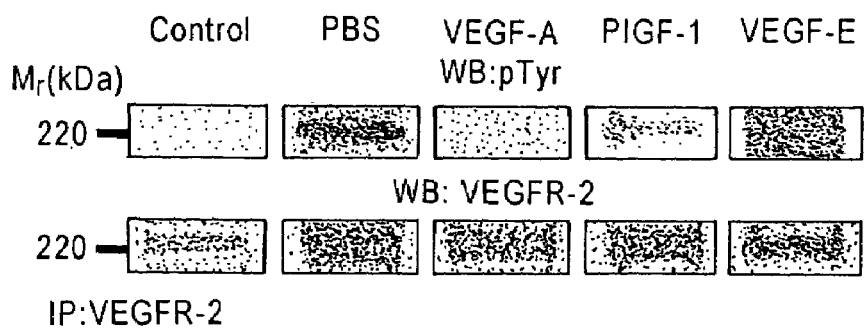
Figure 2D:
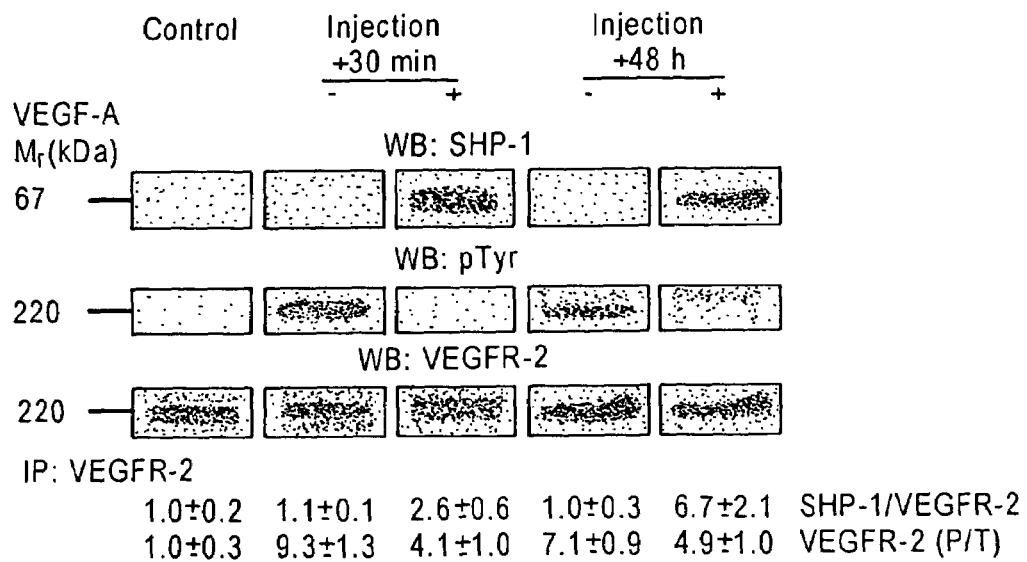
Figure 2E:
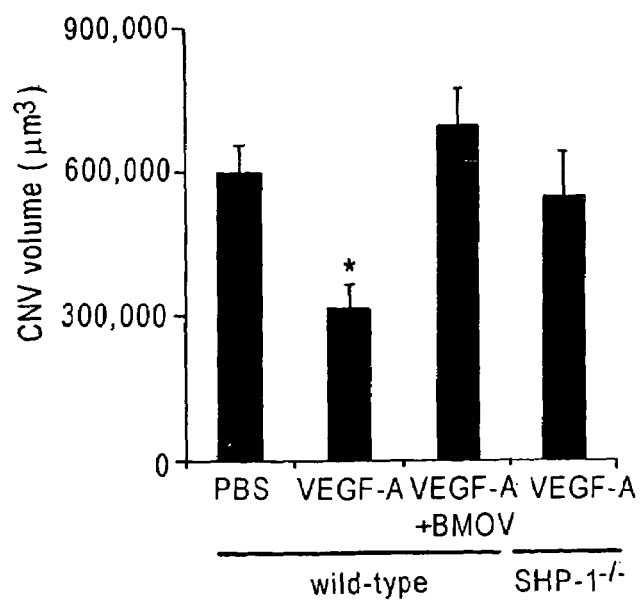
Figure 2F:
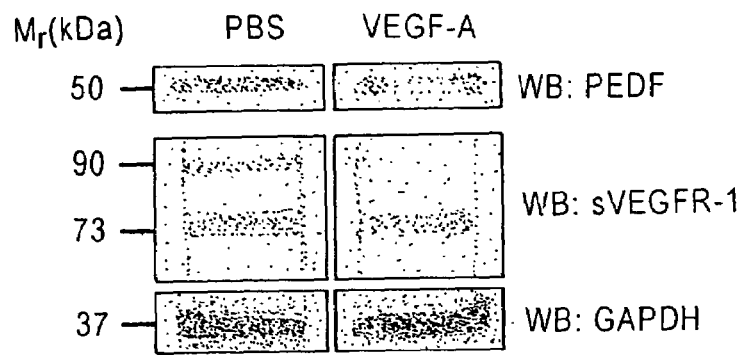

FIG. 2(f) shows that following laser injury, VEGF-A does not induce PEDF or soluble VEGFR-1 isoforms, on day 3. Figure is representative of 3 experiments.

Figure 2G:
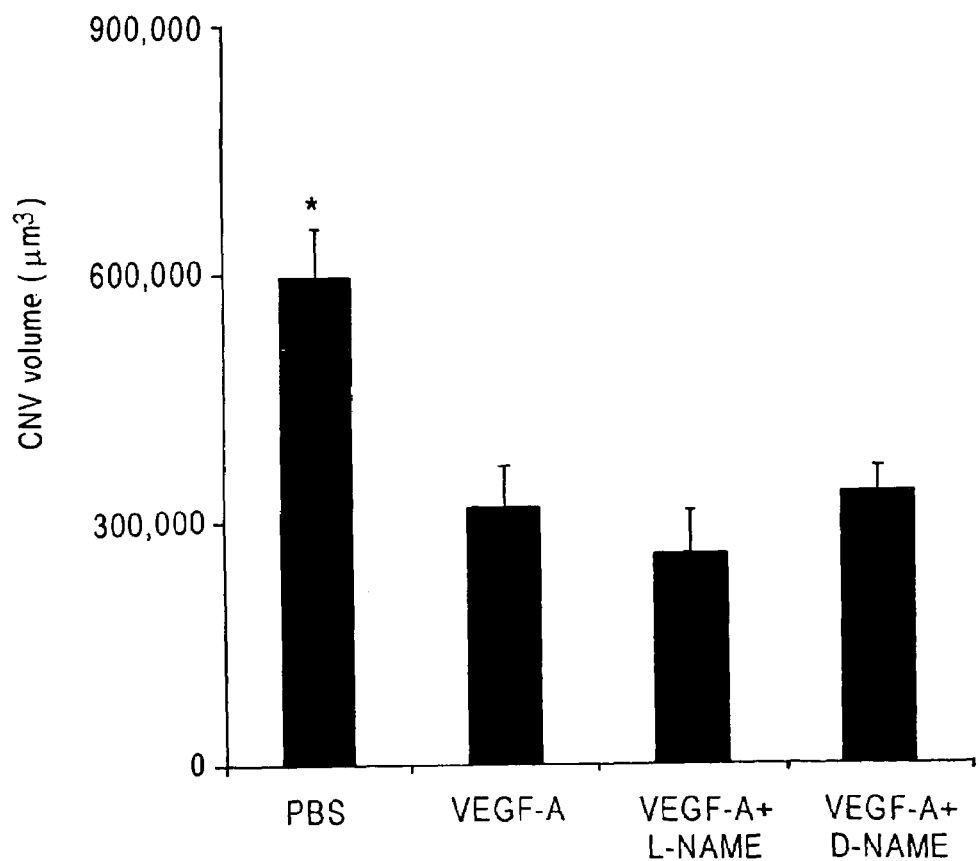

FIG. 2(g) shows that VEGF-A-induced suppression of laser-induced CNV is not affected by nitric oxide synthase inhibition by L-NAME. *P<0.05 compared with VEGF-A (4 ng). n=8-12.

FIG. 3 (a-e) shows that SPARC inhibits VEGFR-1 activation, rerouting VEGF-A signaling. (a) Applied one day before injury, VEGF-A, $CoCl_2$ (0.1 μg) and VEGF-E (4 ng) increase CNV. (b) Constitutive (control) RPE/choroid expression of SPARC is decreased one day after (+1) laser injury and is restored two days after (+2) injury. Figure representative of 3 experiments. (c) CNV inhibition by VEGF-$A_{164}$ applied one day after injury is abolished by SPARC. *P<0.05 compared with PBS. (d) SPARC Ab (4 μg) restores CNV inhibition of VEGF-$A_{164}$, applied one day before or two days after injury. *P<0.05 compared with VEGF-$A_{164}$ alone. (e) VEGF-$A_{164}$ injected 1 day before laser injury increases CNV in SPARC$^{+/+}$ mice but not in SPARC$^{-/-}$ mice. *P<0.05 compared with PBS. VEGF-$A_{164}$ (4 ng).

FIG. 3 (f) shows the percentage of macrophages in the choroid 3 days after laser injury is normalized the value for PBS-treated wild-type (wt) mice. Ccl-2 Ab (1 ng) reduces macrophage numbers both in wt and Vegfr1 tk$^{-/-}$ mice. VEGFR-1 Ab (6 μg) does not reduce macrophage numbers in wt or Ccl2$^{-/-}$ mice. Macrophage numbers are increased PBS-treated Vegfr1 tk$^{-/-}$ mice compared to wt mice. n=5-10. *P<0.05 compared to similarly treated wt mice. #P<0.05 compared to PBS-treatment within genetic group.

FIG. 4(a-f) illustrate that CNV inhibition by VEGF-A is mediated by Ccl-2. (a) Ccl-2 injection abrogates VEGF-$A_{164}$ induced CNV inhibition in wild-type (wt) mice and restores CNV in Ccl2$^{-/-}$ mice. *P<0.05 compared with PBS-treated wt mice. (b) VEGF-$A_{164}$ and PlGF-1 enhance CNV suppression in wild-type (wt), Ccl3$^{-/-}$, and Ccr5$^{-/-}$ mice but not in Ccl2$^{-/-}$ or Ccr2$^{-/-}$ mice. VEGF-E restores CNV in knockout animals. *P<0.05 compared with PBS-injected animals in same genetic group. (c) Clodronate liposome (Clod-LIP)-induced CNV suppression in wild-type mice is not enhanced by VEGF-$A_{164}$ or PlGF-1, but is abolished by VEGF-E. *P<0.05 compared with control (PBS liposome) treated mice. (d) Laser injury does not mobilize CD34$^+$VEGFR-2$^+$ or CD14$^+$CD34$^-$ cells into the peripheral blood. (e) VEGF-$A_{164}$, Ccl-2 Ab, and Clod-LIP decrease the number of BMDEC per eye. Ccl-2 restores BMDEC incorporation following VEGF-$A_{164}$ but not Clod-LIP treatment. *P<0.02 compared with PBS-treated mice. (f) CNV volume following PBS or VEGF-A injection did not vary by whether the fellow eye was injected with PBS (white bars) or VEGF-A (black bars). VEGF-$A_{164}$ (4 ng); PlGF-1: 1.25 μg; VEGF-E: 4 ng; Ccl-2: 0.55 ng; Ccl-2 Ab: 1 ng.

FIG. 5(a-f) illustrates VEGF-A-induced HO-1 decreases Ccl-2 and CNV, and induces cell-cycle arrest. (a,b) HO-1 inhibition with ZnPP abolishes VEGF-A-induced suppression of Ccl-2 secretion 2 days after laser injury (a), and suppression of CNV volume 7 days after laser injury (b). *P<0.05 compared to VEGF-A. n=3 (a), n=9-12 (b). (c) VEGF-$A_{164}$ injection 24 h after laser injury increases HO-1 expression 24 h later. Figure c is representative of 3 independent experiments. (d) Cell cycle distribution in CEC 5 days after laser injury shows $G_0/G_1$ arrest induced by VEGF-A and PlGF-1, but not VEGF-E. n=8. *P<0.05 compared to PBS. (e)

Inhibition of HO-1 by ZnPP reverses $G_0/G_1$ arrest induced by VEGF-A. n=4. *P<0.05 compared to CuPP. (f) Injected 24 h after laser injury, VEGF-$A_{164}$ and PlGF-1, but not VEGF-E, induce p21$^{Cip1/WAF1}$ and decrease cyclin D1 expression 24 h after injection, which are sensitive to HO-1 inhibition. Figure is representative of 3 independent experiments. VEGF-A=VEGF-$A_{164}$ (4 ng); PlGF-1: 1,250 ng; VEGF-E: 4 ng.

Figure 6A:
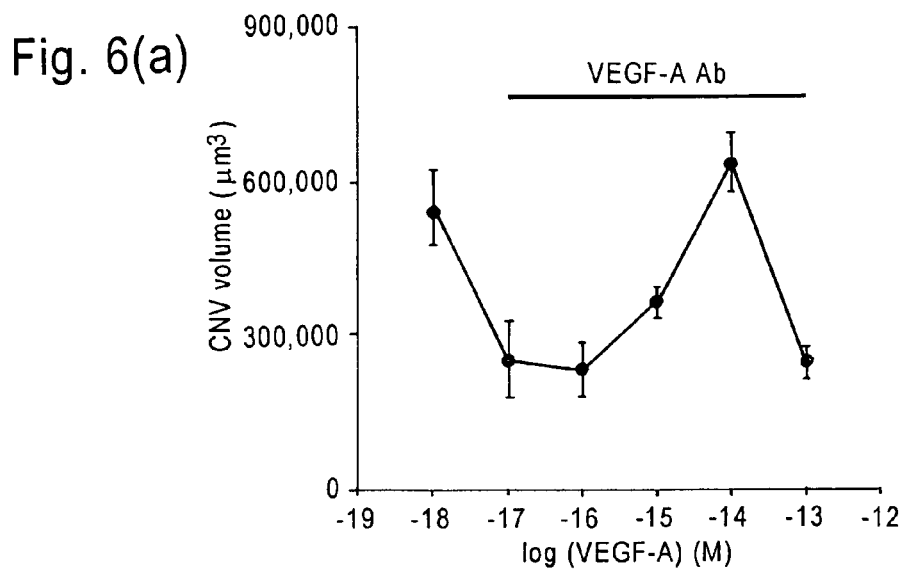

FIG. 6 (a-c) illustrates that (a) In the presence of neutralizing VEGF-A Ab (1 ng on days 0 and 1 after injury), which reduced CNV on day 7, exogenous VEGF-$A_{164}$ exhibited a biphasic effect. (b) Preexisting laser injury created 2 days before subsequent injury led to markedly decreased CNV in the subsequent laser spots near the preexisting injury and slightly decreased CNV in spots far from it. Neutralizing VEGF-A Ab reversed this inhibition in a dose-dependent manner. (c) Preexisting laser injury created 10 days before subsequent injury in wild-type (wt) mice or 2 days before in Vegfr1 tk$^{-/-}$ mice did not affect CNV of subsequent laser spots.

Figure 7A:
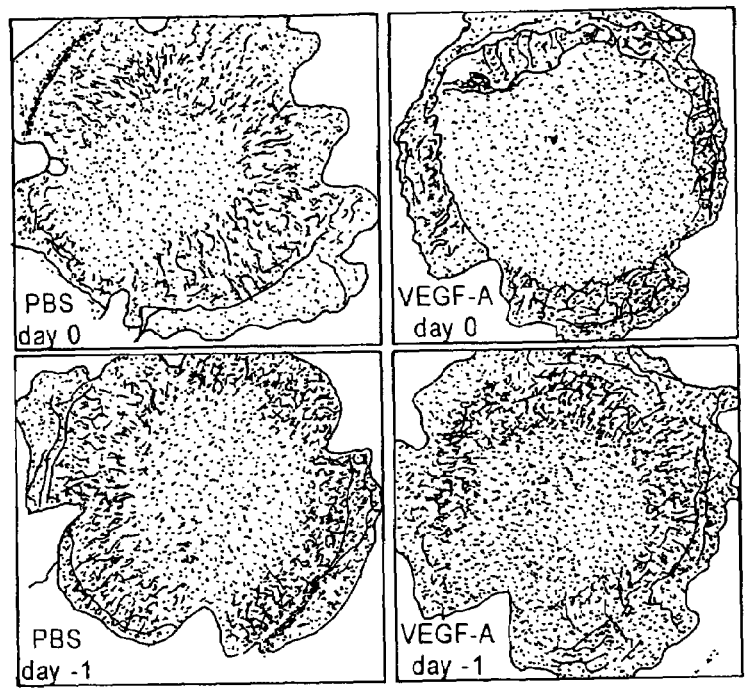
Figure 7B:
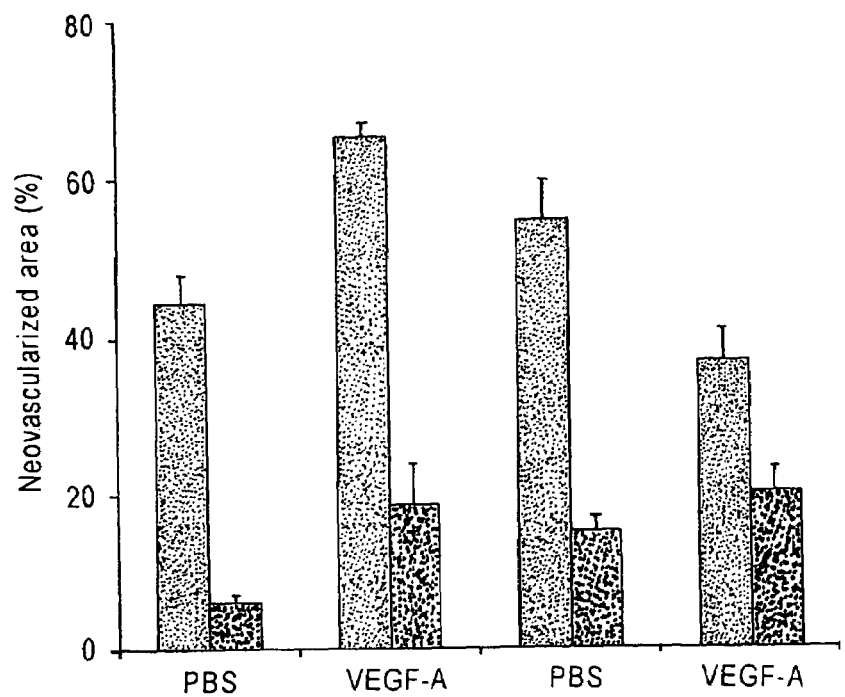

FIG. 7 (a-b) illustrates that corneal neovascularization is increased by pre-injury VEGF-A and reduced by post-injury VEGF-A. (a,b) Representative photographs (a) demonstrating that, compared to PBS, VEGF-$A_{164}$ (1 ng) injected immediately after injury (day 0) reduces (b) hemangiogenesis (green bars) 10 days later compared to PBS, while VEGF-$A_{164}$ (1 ng) injected one day before (left half of picture) injury (day −1) increases it 7 days after (right half of picture) injury, whereas lymphangiogenesis (red bars) is increased by VEGF-A injected before injury, but not reduced by VEGF-A injected after injury. n=8, *P<0.05 compared to PBS.

DETAILED DESCRIPTION

Historically VEGFR-1 was assigned a role as non-signaling decoy receptor because of the low activity and embryonic dispensability of its tyrosine kinase. More recently, its role has become more enigmatic because VEGFR-1 signaling has been reported both to promote and suppress Vascular endothelial growth factor (VEGF)-A-driven angiogenesis. The present invention reveals that VEGF-A and PlGF-1 inhibit inflammatory ocular neovascularization, extending the scope of VEGFR-1 functionality. The present invention reveals the ability of excess VEGF-A to suppress the pro-angiogenic effect of endogenous VEGF-A by interfering with its ability to act through VEGFR-2 and by preventing endothelial cells from responding to mitogenic signals by arresting their proliferation. The "switch" that diverts the injured tissue away from proliferation is driven through VEGFR-1 signaling, which appears to dominate in an environment of excess VEGF-A, in contrast to the usual dominance of VEGFR-2.

VEGF-A promotes inflammation and angiogenesis in many tissues. The present invention reports the unexpected finding that whereas choroidal and corneal neovascularization incited by injury are increased by excess exogenous or endogenous VEGF-A before injury, they are suppressed by VEGF-A after injury. Excess post-injury VEGF-A suppresses neovascularization (hemangiogenesis and vasculogenesis) by inhibiting macrophage recruitment via downregulating the monocyte chemoattractant Ccl-2. Excess post-injury VEGF-A also induces $G_0/G_1$ endothelial cell-cycle arrest by upregulating the cyclin-dependent kinase inhibitor p21$^{Cip1/WAF1}$ and downregulating cyclin D1, without increasing cell death. Endogenous VEGF-A induced by laser-induced CNV also suppresses subsequent development of adjacent CNV. These unorthodox anti-inflammatory and anti-angiogenic effects are mediated via VEGF receptor (VEGFR)-1, which deactivates VEGFR-2 signaling via the phosphatase SHP-1, and through induction of heme oxygenase (HO)-1. Excess VEGF-A meets divergent fates because, at rest, VEGFR-1 activation is silenced by secreted protein, acidic, rich in cysteine (SPARC), which declines transiently after injury, creating a temporal window where VEGF-A signaling is routed principally through VEGFR-1 and VEGF-A levels.

Because inflammation and angiogenesis interact and drive each other in many organs, this invention provides a novel conceptual model of the role of VEGF-A in wound healing. We have shown that tight regulation of VEGF-A following injury permits coordinated orchestration of this response, initiated by arrival of inflammatory cells followed by endothelial proliferation. The transient decline in SPARC immediately following injury temporarily unsilences VEGFR-1 tyrosine kinase activity, promoting VEGF-A signaling via VEGFR-1. Increasing VEGF-A levels during this period not only disrupts leukocyte recruitment by inducing anti-inflammatory pathways via excess VEGFR-1 stimulation, but also arrests endothelial cells, disadvantaging their proliferation in the angiogenesis stage. This Janus-like effect reveals novel therapeutic strategies to modulate angiogenesis in the setting of inflammation and highlights the importance of developing the ability to assay expression of markers such as SPARC to target therapeutics more specifically.

The present invention provides methods of inducing interaction of VEGFR-1 with its ligands and describes a unique mechanism in which VEGF-A acts as a mediator of anti-angiogenesis. The present invention provides methods of inhibiting pathologic ocular angiogenesis and treating and/or preventing ocular neovascularization using agonists of VEGFR-1 signaling, antagonists of VEGFR-2 signaling and VEGF-A, PLGF-1, PLGF-2 and combinations thereof to trigger VEGFR-1 signaling.

As used herein, the term "antibody" refers to an immunoglobulin molecule with a specific amino acid sequence evoked by an antigen, e.g., SPARC, Ccl-2, HO-1, SHP-1 or Ccr-2, and characterized by reacting specifically with the antigen in some demonstrable way. The term "antibody" encompasses polyclonal and monoclonal antibody preparations, CDR-grafted antibody preparations, as well as preparations including hybrid antibodies, altered antibodies, F(AB)'.sub.2 fragments, F(AB) molecules, Fv fragments, single domain antibodies, chimeric antibodies and functional fragments thereof which exhibit immunological binding properties of the parent antibody molecule. The antibodies can also be humanized.

As used herein, the terms "bind" or "binds" or "binding" means any interaction, whether via direct or indirect means, which affects a specified protein, receptor or protein/receptor subunit.

As used herein, the term "carrier" refers to a diluent, adjuvant, excipient, or vehicle with which the compositions of the present invention are administered. The term "pharmaceutically acceptable carrier" refers to a carrier that may be administered to a subject, and which does not destroy the pharmacological activity thereof and is nontoxic when administered in doses sufficient to deliver a therapeutic amount of the compound.

As used herein, "compound" refers to any agent, chemical substance, or substrate, whether organic or inorganic, or any protein including antibodies and functional fragments thereof, peptides, polypeptides, peptoids, and the like.

As used herein, the terms "inhibit(s)" or "downregulate" mean any decrease or reduction in functionality or activity (including, without limitation, angiogenesis, hemangiogenesis, lymphangiogenesis, neovascularization, cell growth or proliferative activity, and inflammation).

As used herein, the terms "interact(s)" or "interacting with" or "interaction with" mean any reactive affect on a specified protein, receptor or protein/receptor subunit by another molecule or subunit, whether through binding, in the whole or in part (e.g., covalent, non-covalent, hydrogen) or signaling, regardless of the affect (e.g., antagonize, inhibit, downregulate, deactivate, interfere, agonize, promote, upregulate, neutralize).

As used herein, the term "introducing" means any means of delivery or administration, whether in vivo or in vitro, including simple contact.

The term "monoclonal antibody" is not limited to antibodies produced through hybridoma technology. The term "monoclonal antibody" refers to an antibody or functional fragment thereof that is derived from a single clone, including any eukaryotic, prokaryotic, or phage clone, and not the method by which it is produced. As used herein, the term "aptamer" means DNA or RNA molecules that have been selected from random pools based on their ability to bind other molecules, like nucleic acid, proteins, small organic compounds, and even entire organisms.

As used herein, the term "neovascular disease" refers to age-related macular degeneration (AMD), including wet AMD (classic, occult, subfoveal, extrafoveal, juxtafoveal) and dry AMD, cancer, choroidal neovascularization, corneal neovascularization, cystoid macular edema, diabetic retinopathy, diabetic macular edema (DME), inflammatory or mechanical macular degeneration, iris neovascularization, myopic macular degeneration, macular degeneration due to histoplasmosis or angioid streaks or inherited retinal or choroidal dystrophies/degenerations, proliferative diabetic retinopathy, psoriasis, retinal neovascularization, vitreal neovascularization, branch/central retinal vein occlusion, retinopathy of prematurity, rheumatoid arthritis, uveitis, or infection.

As used herein, the term "neovascularization" means proliferation of blood vessels in tissue not normally containing them, or proliferation of blood vessels of a different kind than usual in tissue. Non-limiting examples of ocular neovascularization include neovascularization of the choroid (including, classic, occult, Type 1, and Type 2 choroidal), cornea, iris, retina, retinal pigmented epithelium (RPE), and/or vitreous. Ocular neovascularization is also associated with eye neovascular disease such as, for example, AMD, choroidal neovascularization, cystoid macular edema, DME, diabetic retinopathy, inflammatory diabetic retinopathy, retinopathy of prematurity, and traumatic eye injury.

As used herein, the term "receptor" means a structural protein molecule on the cell surface or within the cytoplasm that interacts and/or binds to a ligand.

As used herein, the term "siRNA", "silencing RNA" or "RNAi" refers to RNA that silences or interferes with the expression of certain genes.

As used herein, the term "substantially together" means administering to a subject active ingredients together in the same dosage form, or in separate dosage forms, such that, the active ingredients can be administered either simultaneously or within a period of time such that the subject receives benefit of the aggregate effects of the separate dosage forms. For example, the active ingredients may be taken together or within a few seconds to at least about 24 hours of one another.

As used herein, the terms "upregulate" or "promote" mean any increase in functionality or activity (including, without limitation, angiogenesis, hemangiogenesis, lymphangiogenesis, neovascularization, cell growth or proliferative activity, and inflammation).

As used herein, the term "VEGFR-1 activity" refers to the ability of VEGFR-1 to interact and/or bind VEGF-A, PLGF-1, PLGF-2, VEGF-B or a combination thereof.

As used herein, the term "VEGFR-2 activity" refers to the ability of VEGFR-2 to interact and/or bind to VEGF-A, PLGF-1, PLGF-2, VEGF-C, VEGF-D or a combination thereof.

In a first aspect of the invention, there is provided a method for screening candidate drugs that modulate the VEGF-1 signaling pathway for the treatment or prevention of neovascularization in the eye. Preferably, the test compound induces VEGFR-1 interaction with VEGF-A either by inducing or agonizing VEGFR-1 activity or by inhibiting or antagonizing VEGFR-2 activity. In this aspect of the invention, a test animal, such as a mouse, rat, rabbit, monkey, pig, etc. which has undergone laser photocoagulation of at least one eye to provide injury to the Bruch's membrane is provided. The candidate drug or test compound is administered to the laser treated eye(s) at various times after treatment, preferably within one day to seven days after treatment, more preferably within one to three days after treatment and most preferably on the first day after treatment. The eye is monitored for the appearance or diminution of neovascularization if neovascularization has already begun at the time the test drug is administered. In one embodiment, both eyes are laser photocoagulated and the test compound is administered to only one eye, thereby allowing direct comparison of the effect of the test drug versus no treatment.

In one embodiment, the candidate drug can be pre-screened for its ability to interact with SPARC so as to block the SPARC/VEGFR-1 or SPARC/VEGF-A interactions, neutralize SPARC's silencing of VEGFR-1, inhibit SPARC activity, or otherwise interfere with SPARC inhibition of VEGFR-1 signaling. A method of identifying a modulator of SPARC interacting with VEGFR-1 comprises the steps of: (a) measuring interaction between SPARC and VEGFR-1 in the presence and absence of a test compound under conditions that allow SPARC to silence VEGFR-1, and (b) identifying as a modulator a test compound which alters SPARC silencing of VEGFR-1. Assays known to those skilled in the art include an in vitro cell culture system (of any number of cell types, e.g., human umbilical vein endothelial cells, bovine aortic endothelial cells, human/bovine choroidal endothelial cells, human/mouse RPE cells) where the ability of the test compound to promote tyrosine kinase phosphorylation of VEGFR-1 by VEGF-A or PlGF-1 or PlGF-2 is gauged. Preferably, the compound is an antagonist of SPARC or any substance interfering with SPARC interaction with VEGF-A or VEGFR-1. Candidate drugs for use in the methods and compositions of the present invention include pharmaceutical compounds, small molecules, peptides, proteins, e.g., peptides or proteins that block SPARC, aptamers, e.g., RNA/DNA aptamer, ribozyme, antibodies, functional antibody fragments, and nucleic acids, including oligonucleotides and polynucleotides in sense or antisense orientation, and single or double stranded nucleic acid molecules (e.g., siRNA) that target SPARC sequences and interfere with SPARC gene expression.

In another embodiment, the candidate drug can be screened for its ability to interact with SHP-1 so as to inhibit VEGFR-2 interaction with VEGF-A, neutralize or deactivate VEGF-A, VEGF-C, and/or VEGF-D-mediated VEGFR-2 signaling, inhibit VEGFR-2 activity, or otherwise interfere with and/or block the VEGFR-2 interaction with VEGF-A, VEGF-C, and/or VEGF-D interaction(s). A method for identifying a modulator of SHP-1 inactivation of VEGFR-2 comprises the steps of: (a) measuring interaction between VEGFR-2 and SHP-1 in the presence and absence of a test compound under conditions that allow activation of SHP-1 to inhibit and/or deactivate VEGFR-2, and (b) identifying as a modulator a test compound which alters VEGFR-2 interaction with SHP-1. Assays known to those skilled in the art include an in vitro cell culture system (of any number of cell types, e.g., human umbilical vein endothelial cells, bovine aortic endothelial cells, human/bovine choroidal endothelial cells, human/mouse RPE cells) to measure (1) how much SHP-1 binding to VEGFR-2 is increased using immunoprecipitation and immunoblotting and (2) how much dephosphorylation of VEGFR-2 has occurred using immunoprecipitation and immunoblotting). Preferably, the test compound is an agonist of SHP-1. Candidate drugs for use in the methods and compositions of the present invention include pharmaceutical compounds, small molecules, peptides, proteins, e.g., peptides or proteins that agonize SHP-1, aptamers, e.g., RNA/DNA aptamer, ribozyme, antibodies, functional antibody fragments, and nucleic acids, including oligonucleotides and polynucleotides in sense or antisense orientation, and single or double stranded nucleic acid molecules (e.g., siRNA) that activate SHP-1 sequences and increase SHP-1 gene expression.

In yet another embodiment, the candidate drug can also be screened for its ability to interact with HO-1 so as to inhibit Ccl-2 synthesis, secretion, or activation, inhibit VEGFR-2 activity consequences, or otherwise interfere with and/or block the upregulation of Ccl-2 as a consequence of VEGFR-2 interaction with VEGF-A, VEGF-C, and/or VEGF-D. A method for identifying a modulator of HO-1 inactivation of Ccl-2/MCP-1 to reduce macrophage infiltration comprises the steps of: (a) measuring interaction between Ccl-2 and HO-1 in the presence and absence of a test compound under conditions that allow activation of HO-1 to inhibit and/or deactivate Ccl-2, and (b) identifying as a modulator a test compound which alters Ccl-2 interaction with HO-1. Assays known to those skilled in the art include an in vitro cell culture system (of any number of cell types, e.g., human umbilical vein endothelial cells, bovine aortic endothelial cells, human/bovine choroidal endothelial cells, human/mouse RPE cells) where the ability of the test compound to promote inactivation by HO-1 of Ccl-2/MCP-1 to prevent ocular neovascularization Preferably, the test compound is an agonist of HO-1. Candidate drugs for use in the methods and compositions of the present invention include pharmaceutical compounds, small molecules, peptides, proteins, e.g., peptides or proteins that agonize HO-1, aptamers, e.g., RNA/DNA aptamer, ribozyme, antibodies, functional antibody fragments, and nucleic acids, including oligonucleotides and polynucleotides in sense or antisense orientation, and single or double stranded nucleic acid molecules (e.g., siRNA) that activate HO-1 sequences and increase HO-1 gene expression.

In still another embodiment, the candidate drug can be screened for its ability to interact with Ccl-2 or Ccr-2 so as to block the Ccl-2/Ccr-2 interaction, neutralize Ccl-2 activation of its receptor Ccr-2 (chemokine (C-C motif) receptor-2), inhibit Ccl-2 monocyte chemotaxis or mobilize calcium, or otherwise interfere with Ccl-2 activation of its receptor, Ccr-2. Ccl-2, chemokine (C-c motif) ligand 2 is also known by several alias: HC11; monocyte chemotactic and activating factor (MCAF); monocyte chemoattractant protein-1 (MCP1 or MCP-1); SCYA2; GDCF-2; SMC-CF; MGC9434; and GDCF-2 HC11.

Candidate drugs for use in the methods and compositions of the present invention include pharmaceutical compounds, small molecules, peptides, proteins, e.g., peptides or proteins that block Ccl-2 or CCR2, aptamers, e.g., RNA/DNA aptamer, ribozyme, antibodies, functional antibody fragments, and nucleic acids, including oligonucleotides and polynucleotides in sense or antisense orientation, and single or double stranded nucleic acid molecules (e.g., siRNA) that target Ccl-2 and/or Ccr-2 sequences and interfere with Ccl-2 gene expression or that target Ccr2 and interfere with Ccr2 gene expression. Exemplary compounds that inhibit Ccl-2 binding to its receptor, Ccr-2, include those disclosed in U.S. Pat. Nos. 6,653,345; 6,677,365; 6,670,364; and 6,534,521, for example. Exemplary compounds that target Ccr-2 and inhibit Ccl-2 interaction with Ccr-2 include the ligands disclosed in J. Med. Chem., 2003, 46:4070-4086. Preferred compounds that either neutralize Ccl-2 activity or otherwise inhibit Ccl-2 binding to Ccr-2 include monoclonal antibodies and functional fragments thereof.

Alternatively, any one of the candidate drugs can first be screened in the animal model and those compounds that exhibit an inhibitory effect on neovascularization can then be further screened to determine their effect on SPARC and/or VEGFR-1, SHP-1 and/or VEGFR-2, HO-1 and/or VEGFR-2, and/or Ccl-2 and/or Ccr-2.

The test compound may be administered to the test animal intravitreously (e.g., by injection or sustained delivery implant), transsclerally or topically, and preferably by topical application to the affected eye(s) of the animal. Treated animals are periodically examined to determine the effect of the candidate drug on angiogenesis. A decrease in number of macrophages or a decrease of neovascularization in the treated eye, for example, is an indication of the ability of the candidate drug to effectively treat neovascularization associated with eye pathologies.

Compounds that demonstrate an inhibitory effect on, for example, SPARC silencing VEGFR-1 activity, SHP-1 inhibiting VEGFR-2 activity, HO-1 inhibiting Ccl-2, Ccl-2/Ccr-2 interaction, or neovascularization of the injured eye can be further tested to determine their respective effect by any assay for SPARC activity, e.g., SPARC ability to silence VEGFR-1 or ability to interact with VEGFR-1.

In a preferred embodiment of this aspect of the invention the test compound is an antibody or functional antibody fragment, most preferably a humanized antibody or functional fragment thereof. Antibodies can be developed by known methods in the art against the SPARC, protein. The antibodies may be polyclonal antibodies or monoclonal antibodies.

Polyclonal antibodies to SPARC can be produced by, for example, administering purified SPARC, preferably human SPARC, to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies to SPARC can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties).

In another embodiment, SPARC activity and/or SPARC/VEGFR-1 and/or SPARC/VEGF-A interactions, in the eye is inhibited with blocking peptides that interact specifically with and inhibit the active site of SPARC, thereby inhibiting or interfering with SPARC silencing of VEGFR-1.

The SPARC blocking peptides of the invention can be produced by chemical synthesis in accordance with art recognized methods and also by incorporating a nucleic acid molecule, encoding the blocking peptide into an expression vector, introducing the expression vector into a host cell and expressing the nucleic acid molecule to yield polypeptide. The polypeptide can then be recovered and purified by any applicable purification method, including ammonium sulfate or ethanol precipitation, acid extraction, anion or cation exchange chromatography, gel filtration, hydrophobic interaction chromatography, affinity chromatography, hydroxyapatite chromatography, and high performance liquid chromatography ("HPLC").

SPARC blocking peptides can also be produced in vivo, for example by delivering a vector containing a DNA molecule encoding a SPARC blocking peptide operationally linked to an expression cassette to the eye, in accordance with the methods of the invention described herein.

In another aspect of the invention there is provided methods of measuring SPARC as a means to determine a course of treatment for choroidal or corneal neovascularization, angiogenesis, cell proliferation and inflammation. Low or reduced levels of SPARC is indicative that VEGF-A, PLGF-1, PLGF-2 or combinations thereof could be used to treat or inhibit angiogenesis as VEGF-A, PLGF-1 or PLGF-2 signaling would be principally routed through VEGFR-1. High or raised levels of SPARC would indicate that VEGF-A, PLGF-1 or PLGF-2 would not be effective in inhibiting angiogenesis as their signaling would be principally routed through VEGFR-2.

In one embodiment, a method for determining a course of treatment for ocular neovascularization comprises measuring the amount of SPARC in an eye of a subject in need thereof, comprising: (1) introducing into the vitreous of an eye an antibody conjugated to a fluorescent label that binds to SPARC, (2) measuring the amount of fluorescence in the eye, and (3) determining the course of treatment based on the results, wherein a low or reduced level of SPARC is indicative that VEGF-A, PLGF-1, and/or PLGF-2 would be principally routed through VEGFR-1, and a high or increased level of SPARC is indicative that VEGF-A, PLGF-1, and/or PLGF-2 would be principally routed through VEGFR-2. In another embodiment, the method for measuring the amount of SPARC comprises: (1) taking a sample of vitreous or subretinal fluid from an eye of a subject in need thereof, (2) introducing into the sample an antibody conjugated to a fluorescent label that binds to SPARC, and (3) measuring the amount of fluoresecense in the sample. In another embodiment, there is a method to assess SPARC levels in the choroid/RPE of the eye comprising, introducing a SPARC antibody or other small molecule (e.g., aptamer) that binds to SPARC, coupled with a fluorescent reporter dye, (intravenously) into of the eye, and imaging the eye for this fluorescent signal by angiography. The method of introduction may be intravenously or intraocularly (e.g., intravitreously by injection or delivery implant). These methods for determining a course of treatment are not limited to the eye, but may be applied to other tissues which would benefit from optimizing VEGF-A/VEGFR-1 interaction.

In another aspect of the invention there is a method of determining a dosage amount of an anti-VEGF-A therapy for a subject in need thereof, comprising measuring intraocular, subretinal and/or choroidal levels of SPARC and VEGF-A. Low or reduced levels of SPARC and high or raised levels of VEGF-A, relative to a normal individual, are indicative that the dosage amount of anti-VEGF drugs should be decreased. High or raised levels of SPARC and low or reduced levels of VEGF-A, relative to a normal individual, are indicative that the dosage amount of anti-VEGF drugs should be increased. Anti-VEGF-A therapies include Macugen®, Lucentis™ (Genentech, Inc.) and VEGF-Trap.

In another aspect of the invention there are compounds that demonstrate an agonistic effect on SHP-1 inhibiting VEGFR-2 activity, and/or HO-1 inhibiting Ccl-2 activity. Neovascularization of an injured eye can be tested to determine the effects of compounds, preferably agonistic compounds, on SHP-1 and/or HO-1 by any assay for SHP-1 and/or HO-1 activity, e.g., SHP-1 to bind and inhibit VEGFR-2 activity, and/or HO-1 to interact with and inhibit Ccl-2 activity, as described herein.

Therapeutic Compositions and Methods

In another aspect of the invention, there is provided methods and compositions for preventing and treating ocular angiogenesis and neovascularization associated with eye neovascular disease such as choroidal neovascularization, diabetic retinopathy, retinopathy of prematurity, diabetic macular edema, corneal neovascularization, iris neovascularization, retinal neovascularization and vitreal neovascularization, and traumatic eye injury.

Methods of treatment and/or prevention of the present invention comprise administering to a subject in need thereof VEGF-A, PLGF-1, PLGF-2 or a combination thereof. In one embodiment, the VEGF-A may be administered to a patient, preferably a mammal, most preferably a human, suffering from traumatic eye injury after eye injury but prior to macrophage recruitment. The window of time in which to administer VEGF-A, PLGF-1 or a combination prior to macrophage recruitment is about 24 hours after ocular injury. Ocular injury may have been laser induced, or caused by chemical, mechanical or physical trauma. Any VEGF-A or PLGF-1 may be used, including VEGF-$A_{110}$, VEGF-$A_{120}$, VEGF-$A_{121}$, VEGF-$A_{144}$, VEGF-$A_{145}$, VEGF-$A_{164}$, VEGF-$A_{165}$, VEGF-$A_{188}$, VEGF-$A_{189}$, VEGF-$A_{205}$, VEGF-$A_{206}$. Preferably, VEGF-$A_{165}$, VEGF-$A_{121}$, or a combination thereof is administered topically or by direct injection. Most preferably, VEGF-$A_{165}$ is administered.

In another embodiment, the VEGF-A, PLGF-1 and/or PLGF-2 may be administered substantially together with a compound that induces VEGFR-1 activity, either by inhibition of SPARC or by inhibition of VEGFR-2 signaling or activity. VEGF-A, PLGF-1, PLGF-2 or a combination thereof may be administered substantially together with SPARC antagonist and/or a VEGFR-2 signaling-inhibiting molecule. There is a method of inducing VEGFR-1 by inhibiting the VEGF-C and/or VEGF-D interaction with VEGFR-2 signaling pathway.

In another embodiment, VEGF-A, PLGF-1, PLGF-2 or a combination thereof may be administered substantially together with and/or Ccl-2 and/or Ccr-2 antagonist. Such antagonist may be HO-1. Such antagonist may be a Ccl-2 blocking peptide. Ccl-2 activity and/or Ccr-2/Ccl-2 interaction in the eye is inhibited with Ccl-2 blocking peptides that bind specifically to and inhibit the active site of Ccl-2 or Ccr-2 blocking peptides that inhibit or interfere with Ccl-2 binding and/or activation of Ccr-2. Human Ccl-2 is secreted as a 76 amino acid protein. Chemical synthesis of Ccl-2 analogues has revealed that the amino-terminal residues 1-6 are important for receptor recognition and signaling, and modification or removal of the amino terminal region can completely inactive these chemokines. Proost et al., (1998) J. Immun. 160: 4034-41. Examples of amino-terminal truncated versions of Ccl-2 useful in the practice of this invention include the following Ccl-2 blocking peptides: (Ccl-2 residues 7-76), (Ccl-2 residues 8-76), (Ccl-2 residues 9-76), and any Ccl-2 truncation lacking amino acid residues 2-8 (and including residues 1 and 9-76). In one embodiment of this aspect of the invention, the Ccl-2 antagonist is Ccl-2 lacking amino acids 2-8.

Other examples of blocking peptides useful in the practice of this invention include any peptides that block the activity of Ccl-2, including for example, amino terminal deletions of Ccl-2. Studies have shown that amino-terminal truncations of Ccl-2, such as, for example, an Ccl-2 truncation (including amino acid residues 6-76 of Ccl-2) can completely block the chemotactic effect of Ccl-2 on monocytes (Proost, supra). Other examples of useful peptide antagonists include Ccl-2 fusion peptides, amino terminal modifications of Ccl-2 such as N-terminal methylation, amino acid substitutions, glycosylation, proteolytic cleavage, and linkage to an antibody molecule or other cellular ligand.

The Ccl-2 blocking peptides useful in the invention can be produced by chemical synthesis in accordance with art recognized methods and also by incorporating a nucleic acid molecule, encoding the blocking peptide into an expression vector, introducing the expression vector into a host cell and expressing the nucleic acid molecule to yield polypeptide. The polypeptide can then be recovered and purified by any applicable purification method, including ammonium sulfate or ethanol precipitation, acid extraction, anion or cation exchange chromatography, gel filtration, hydrophobic interaction chromatography, affinity chromatography, hydroxyapatite chromatography, and high performance liquid chromatography ("HPLC").

Ccl-2 blocking peptides can also be produced in vivo, for example by delivering a vector containing a DNA molecule encoding a Ccl-2 blocking peptide operationally linked to an expression cassette to the eye, in accordance with the methods of the invention described herein.

Compounds that interfere with Ccr-2 binding of Ccl-2 are also useful as Ccl-2/Ccr-2 antagonists in the practice of the invention. Anti-Ccr-2 antibodies, such as the humanized Ccr-22 antibodies of U.S. Pat. No. 6,696,550, and U.S. Pat. No. 6,084,075 are useful in the practice of the present invention.

In yet another embodiment, the VEGF-A, PLGF-1, PLGF-2 or combination thereof may be administered substantially together with a SHP-1 agonist and/or HO-1 agonist. Preferably, the compound or combination of compounds inducing VEGFR-1 activity is administered prior to administration of VEGF-A, PLGF-1, PLGF-2 or a combination thereof.

In another embodiment, VEGF-A, PLGF-1, PLGF-2 or a combination thereof may be administered to a patient having reduced SPARC/VEGFR-1 interaction, which reduced interaction is determined by methods described herein. In another embodiment, VEGF-A, PLGF-1, PLGF-2 or a combination thereof may be administered to a patient with reduced macrophage recruitment.

In another aspect of the invention, there is provided methods and compositions for modulating stem cell incorporation into an area of neovascularization by reducing Ccl-2 activity. In a preferred embodiment, Ccl-2 activity is reduced by administering to a subject in need thereof a therapeutically effective amount of VEGF-A, PLGF-1, PLGF-2, or a combination thereof. In another preferred embodiment, Ccl-2 activity is increased to promote stem cell incorporation in conditions such as inherited retinal or choroidal degenerations including, but not limited to, retinitis pigmentosa.

In yet another aspect of the invention, there is provided a method for selectively inhibiting hemangiogenesis (blood vessels), but not substantially inhibiting lymphangiogenesis (lymph vessels). Such methods are beneficial in treating conditions where both hemangiogensis and lymphangiogenesis both coincide, such as ocular neovascularization and cancer, because where reduction in blood vessels may be desirable, lymphatic vessel maintenance may be beneficial in removing the proteins/toxins released into the tissue by the abnormal blood vessels. Methods comprise administering to the eye of a subject in need thereof a therapeutically effective amount of VEGF-A, PLGF-1, PLGF-2, or a combination thereof.

The SPARC, Ccl-2, and/or Ccr-2 inhibitory agents, SHP-1 and/or HO-1 agonists, VEGF-A, PLGF-1, PLGF-2, and any combinations thereof may be administered with a pharmaceutically acceptable carrier. Such pharmaceutical carriers can be sterile liquids, such as water and oils, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Suitable pharmaceutical excipients include starch, glucose, lactose, sucrose, gelatin, malt, rice, sodium stearate, glycerol monostearate, glycerol, propylene, glycol, water, and the like. The composition, if desired, can also contain minor amounts of wetting or emulsifying agents, or pH buffering agents. The SPARC, Ccl-2, and/or Ccr-2 inhibitory agents, SHP-1 and/or HO-1 agonists, and any combinations thereof or other active agents of the composition may be encased in polymers or fibrin glues to provide controlled release of the active agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for injection into the eye Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Compositions of the invention may be administered to the affected eye(s) of a subject by transscleral delivery for example by passive diffusion, controlled release device with or without a remote on-demand delivery system, osmotic pump, or via an implant in the eye, preferably a sustained release implant in the posterior of the eye.

In another preferred embodiment, the composition is administered by topical application to the eye. The compositions are typically administered to the affected eye by applying one to four drops of a sterile solution or suspension, or a comparable amount of an ointment, gel or other solid or semisolid composition, to the surface of the affected eye one to four times per day. However, the compositions may also be formulated as irrigating solutions that are applied to the affected eye during surgical procedures.

The ophthalmic compositions of the present invention will contain one or more SPARC inhibitors, one or more Ccl-2 inhibitors, one or more Ccr-2 inhibitors, one or SHP-1 agonist, one or more HO-1 agonist, one or more anti-inflammatory agents, or combinations thereof in pharmaceutically acceptable vehicles. For example, the ophthalmic compositions of the present invention may contain one or more Ccl-2 inhibitors and/or Ccr-2 inhibitors in combination with one or a combination of a steroid drug, such as triamcinolone, fluocinolone, anecortave acetate, dexamethasone and combinations thereof; or a non-steroidal anti-inflammatory drug, such as celecoxib, flurbiprofen, and aspirin, for example.

Topical compositions will typically have a pH in the range of 4.5 to 8.0. The ophthalmic compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

Ophthalmic pharmaceutical products are typically packaged in multidose form. Preservatives are thus included to prevent microbial contamination during use. Suitable preservatives include: polyquaternium-1, benzalkonium chloride, thimerosal, chlorobutanol, methyl paraben, propyl paraben, phenylethyl alcohol, edetate disodium, sorbic acid, or other agents known to those skilled in the art. The use of polyquaternium-1 as the antimicrobial preservative is preferred. Typically such preservatives are employed at a level of from 0.001% to 1.0% by weight.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g., Pluronic F-68, F-84 and P-103), cyclodextrin, or other agents known to those skilled in the art. Typically such co-solvents are employed at a level of from 0.01% to 2% by weight.

The use of viscosity enhancing agents to provide the topical compositions of the invention with viscosities greater than the viscosity of simple aqueous solutions may be desirable to increase ocular absorption of the active compounds by the target tissues or increase the retention time in the eye. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

The SPARC, Ccl-2, and/or Ccr-2 inhibitory agent-containing, and/or SHP-1 and/or HO-1 agonist-containing compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the active agents of the compositions of the invention which will be effective in the treatment, inhibition and/or prevention of neovascularization of the eye can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Various delivery systems are known and can be used to administer a composition of the invention, e.g., encapsulation in liposomes, microparticles, microcapsules, recombinant cells capable of expressing the compound, receptor-mediated endocytosis (See, e.g., Wu and Wu, J. Biol. Chem. 262:4429-4432 (1987)), construction of a nucleic acid as part of a retroviral or other vector, etc. The compounds or compositions may be administered together with other biologically active agents. Administration is preferably local, either on the surface of the affected eye(s) or injected into the affected eye(s).

Local administration to the affected eye(s) may be achieved by, for example, and not by way of limitation, local infusion during surgery, topical application, e.g., in conjunction with a wound dressing after surgery or via drops or application of a gel or other topical solution, by injection, or by means of an implant, said implant being of a porous, non-porous, or gelatinous material, including membranes, such as sialastic membranes, or fibers. Preferably, when administering a protein, including an antibody or functional fragment thereof, of the invention, care must be taken to use materials to which the protein does not absorb.

In another embodiment, the compound or composition can be delivered in a vesicle, in particular a liposome. See Langer, Science 249:1527-1533 (1990); Treat et al., *Liposomes in the Therapy of Infectious Disease and Cancer*; Lopez-Berestein and Fidler (eds.), Liss, New York, pp. 353-365 (1989); Lopez-Berestein, ibid., pp. 317-327.

In yet another embodiment, the compound or composition can be delivered in a controlled release system. In one embodiment, a pump may be used. See Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used (see Langer and Wise (eds.), *Medical Applications of Controlled Release*, CRC Pres., Boca Raton, Fla. (1974); Smolen and Ball (eds.), *Controlled Drug Bioavailability, Drug Product Design and Performance*, Wiley, New York (1984); Ranger and Peppas, J., Macromol. Sci. Rev. Macromol. Chem. 23:61 (1983); Levy et al., Science 228:190 (1985); During et al., Ann. Neurol. 25:351 (1989); Howard et al., J. Neurosurg. 71:105 (1989)). In yet another embodiment, a controlled release system can be placed in proximity of the eye.

The following examples are presented for the illustrative purposes and it is to be understood that the present invention is not limited to those precise embodiments, and that various changes and modifications can be effected therein by one skilled in the art without departing from the scope and spirit of the invention as defined by the appended claims.

Example 1

VEGF-A Downregulates Ccl-2 and Inhibits CNV In Vivo

We tested the effect of injecting murine VEGF-$A_{164}$ (the murine homolog of VEGF-$A_{165}$) into the vitreous cavity of mice following laser injury. Laser injury fractures Bruch membrane (BrM), the extracellular matrix between the retinal pigmented epithelium (RPE) and choroid, the highly vascular tissue beneath the RPE. The ensuing inflammation triggers proliferation of choroidal endothelial cells (CEC) that then migrate through these fractures, resulting in choroidal (subretinal) neovascularization (CNV). Ryan, S. J. *Subretinal neovascularization. Natural history of an experimental model.* (1982) Arch Ophthalmol 100, 1804-9; Tobe, T. et al. *Targeted disruption of the FGF2 gene does not prevent choroidal neovascularization in a murine model.* (1998) Am J Pathol 153, 1641-6). This process is driven by upregulated secretion of Ccl2 that peaks 2 days after injury, leading to recruitment of macrophages into the choroids that peaks 3 days after injury. Sakurai, E., Anand, A., Ambati, B. K., van Rooijen, N. & Ambati, J. *Macrophage depletion inhibits experimental choroidal neovascularization.* (2003) Invest Ophthalmol Vis Sci 44, 3578-85; Espinosa-Heidmann, D. G. et al. *Macrophage depletion diminishes lesion size and severity in experimental choroidal neovascularization.* (2003) Invest Ophthalmol Vis Sci 44, 3586-92.

Figure 1A:
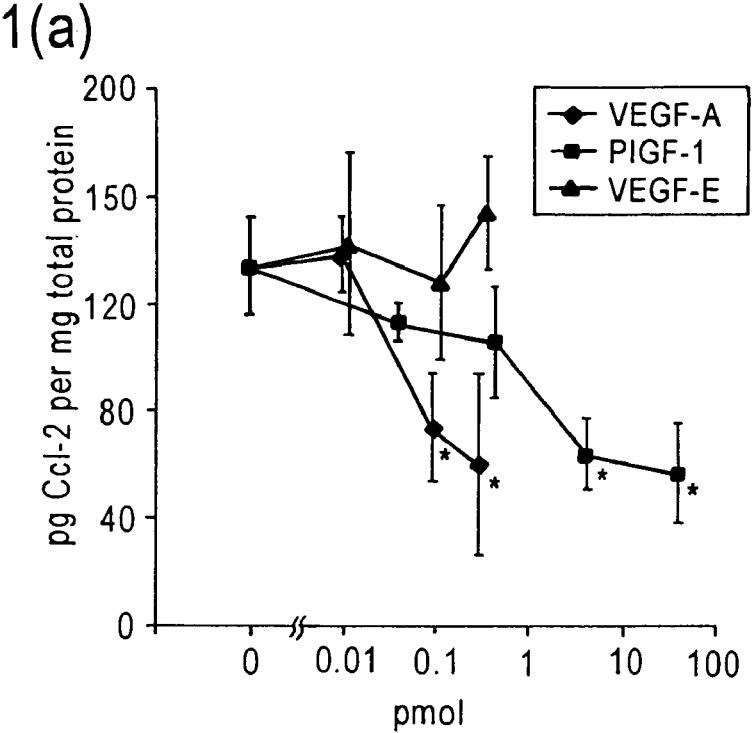
FIG. 1($a$-$c$) illustrate VEGFR-1 ligands suppress CNV by inhibiting Ccl-2 and macrophage recruitment. VEGF-A and PlGF-1, but not VEGF-E, suppress maximal Ccl-2 expression in the RPE and choroid on day 2 (a), the number of macrophages (percentage of all cells) in the choroid on day 3 (b), and the volume of CNV on day 7 (c). VEGF-E (triangle) and PlGF-1 (square) together, and VEGF-$A_{164}$ (circle) and VEGF-E (triangle) together (single data points depicted as dotted lines) suppressed CNV volume similar to PlGF-1 or VEGF-$A_{164}$ alone, respectively. VEGF-E and FGF-2 induce minor increases in CNV volume (c). *$P<0.01$, #$P<0.05$ compared to PBS. §$P<0.01$ compared to VEGF-E and >0.90 compared to PlGF-1. ^$P<0.01$ compared to VEGF-E and >0.90 compared to VEGF-$A_{164}$.
FIG. 1e illustrates that CNV inhibited by $CoCl_2$ (0.1 μg) and $H_2O_2$ (0.1 μg) is abrogated by VEGF-$A_{164}$ antibody (1 ng). *P<0.05 compared to PBS.
FIG. 1f illustrates that VEGFR-1 Ab (6 μg), but not VEGFR-2 Ab (250 ng), abrogates inhibition of CNV by $CoCl_2$ and VEGF-$A_{164}$. *P<0.05 compared to drug alone.
FIG. 1g illustrates the blockade of tyrosine kinase activity of VEGFR-1 by SU5416 (0.3 ng), but not that of VEGFR-2 by SU1498 (3.5 ng) or of PDGF-R by AG1295 (1.5 ng), abrogates VEGF-$A_{164}$-induced suppression of CNV.
FIG. 1h illustrates CNV is increased in PBS-treated Vegfr1 tk$^{-/-}$ mice compared to wild-type (wt) mice, and VEGF-A does not reduce CNV in Vegfr1 tk$^{-/-}$ mice. *P<0.05 compared to PBS-treated wt mice. #P<0.05 compared to PBS-treated mice in same genetic group. (a,b), n=9-18 (c-f). Scale bar 100 μm (d).
FIG. 1(k) illustrates VEGF-A levels in the RPE/choroid following laser injury with or without injection of VEGF-$A_{164}$ or $CoCl_2$ immediately after injury. Peak VEGF-A following VEGF-$A_{164}$ injection is 1.5±0.3 ng/ml (total protein in RPE/choroid of 2.9±0.2 mg/ml).
FIG. 1(l) illustrates VEGF-A-induced CNV suppression is reversed by DBAPBA in a dose-dependent fashion. *P<0.05 compared with VEGF-A alone.
FIG. 1(m) illustrates that neither NP-1 and NP-2 Abs nor control goat (gt) or rabbit (rb) IgG abolish VEGF-$A_{164}$-induced suppression of CNV. *P<0.05 compared with VEGF-$A_{164}$. n=3
Figure 1B:
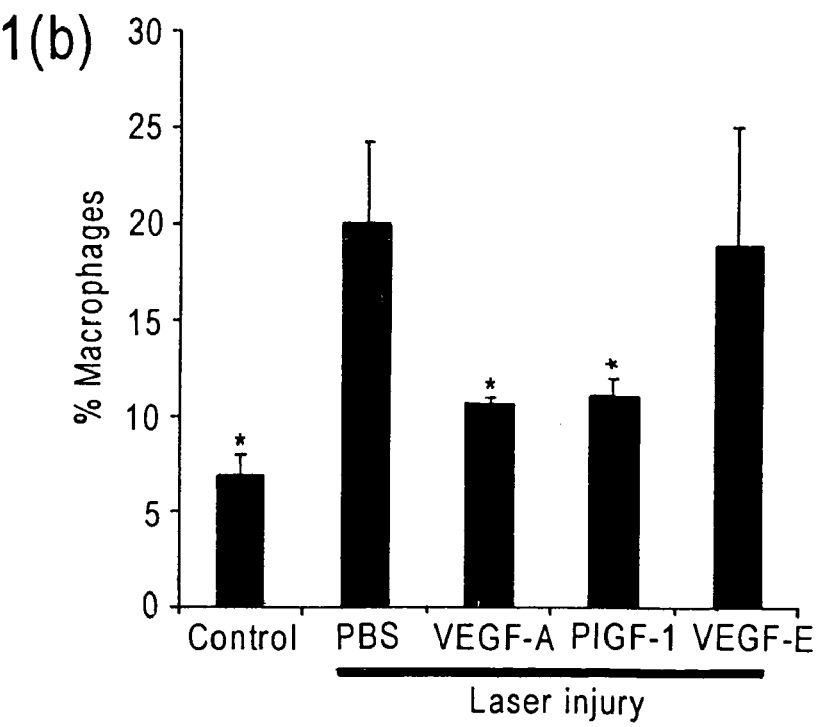
Figure 1C:
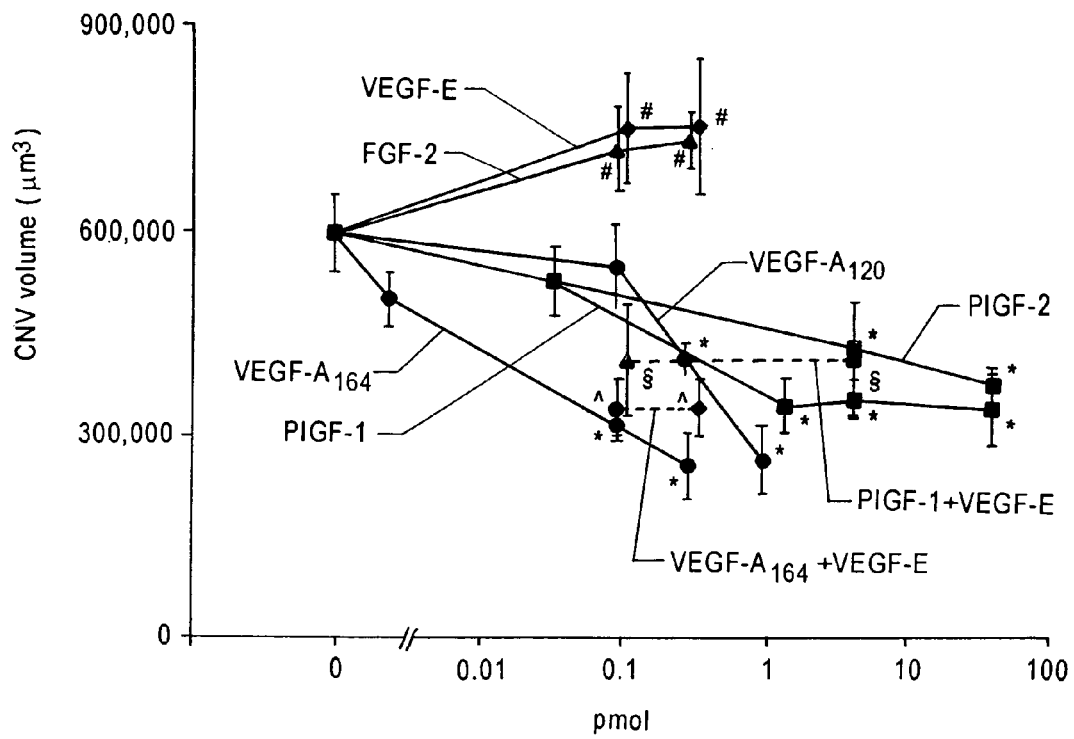
Figure 1D:
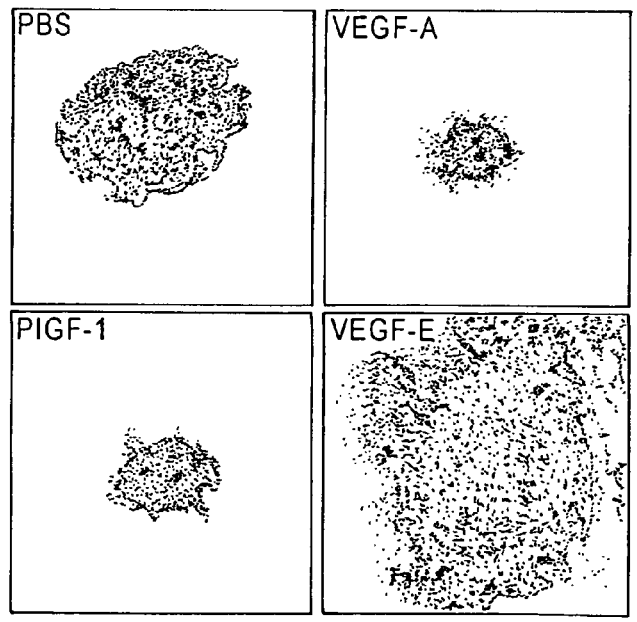
Figure 1E:
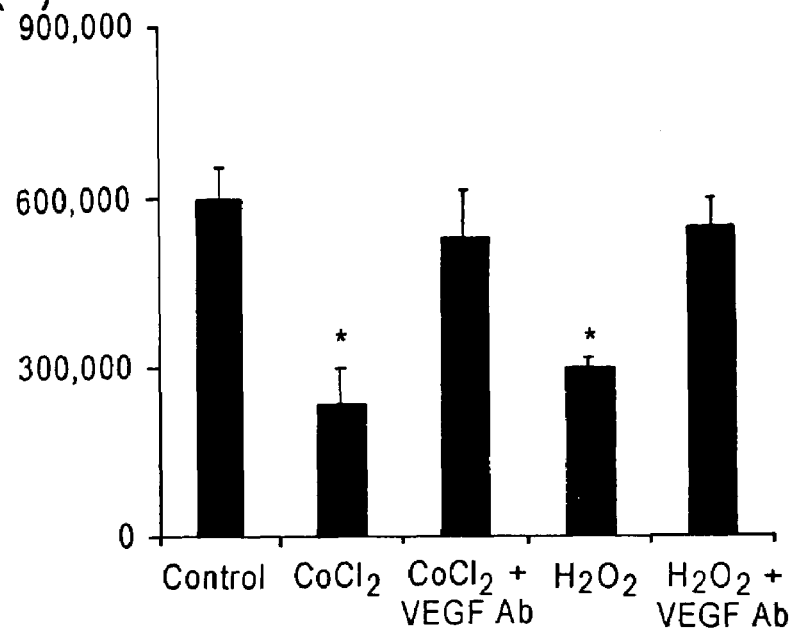
Figure 1F:
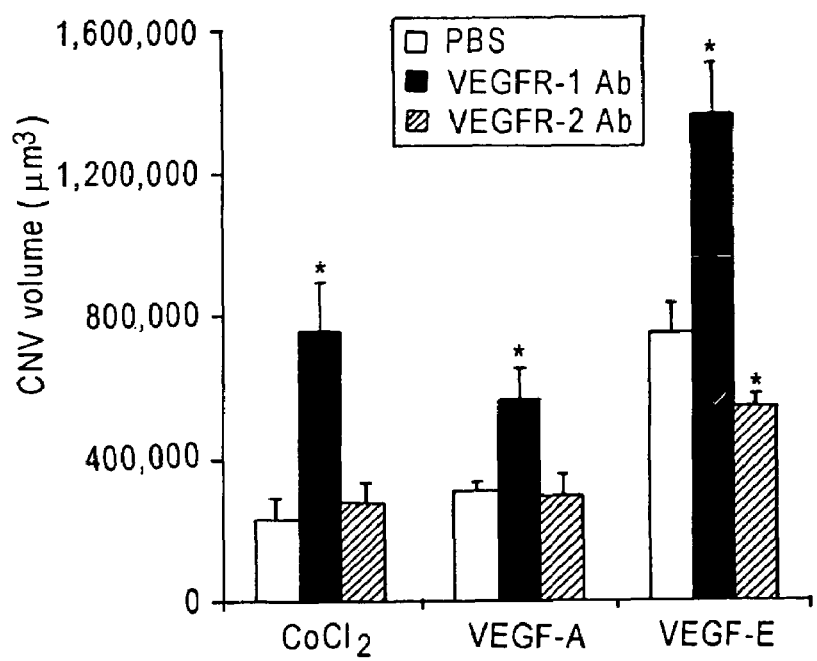
Figure 1G:
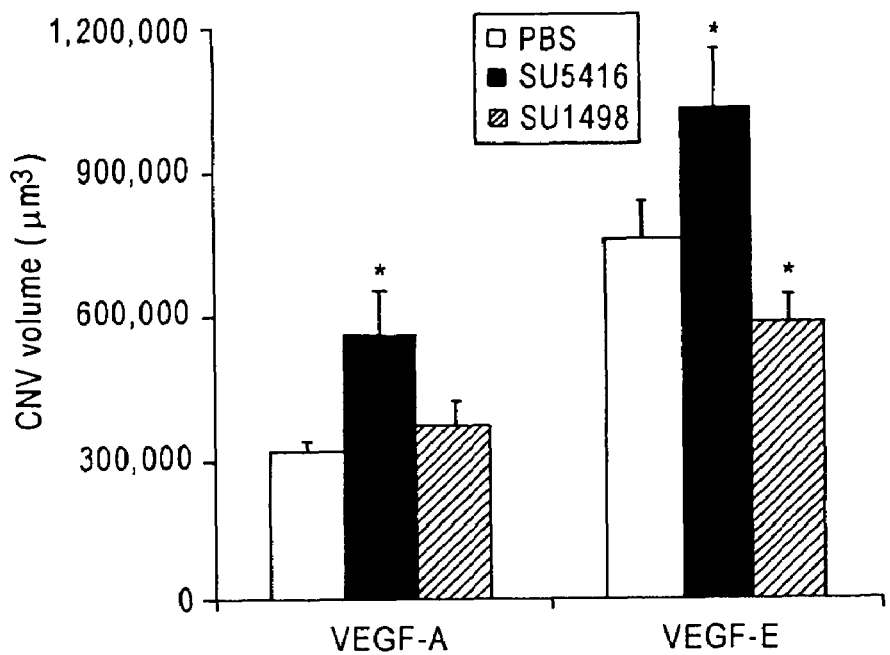
Figure 1H:
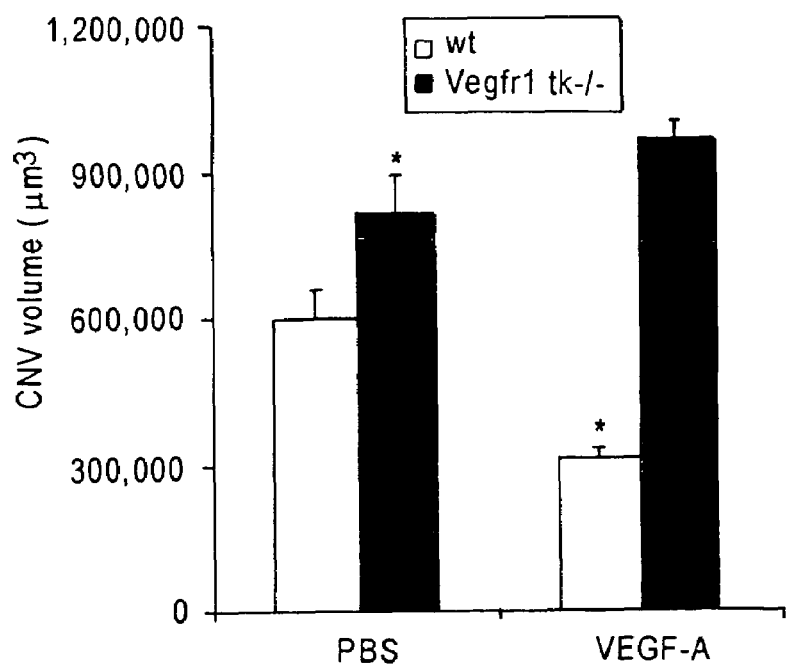
Figure 1I:
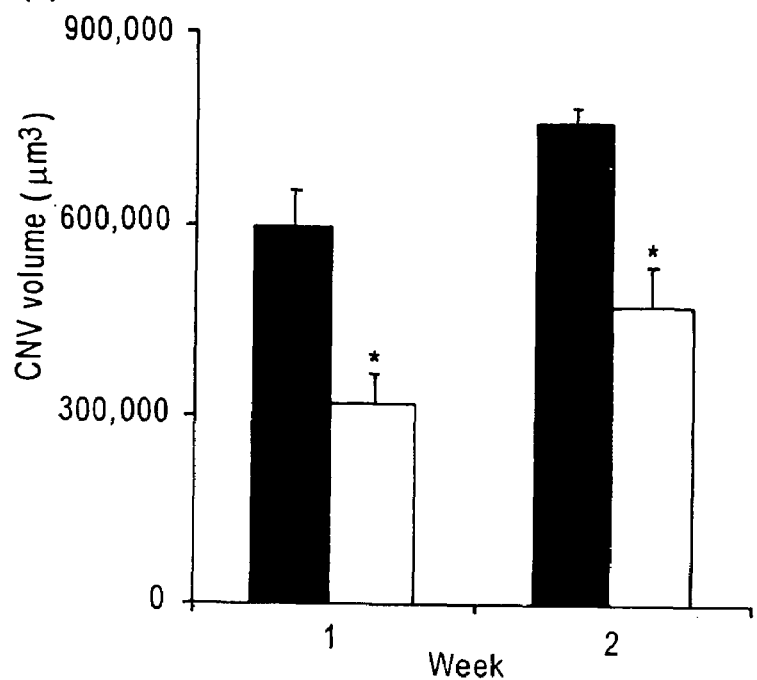
Figure 1J:
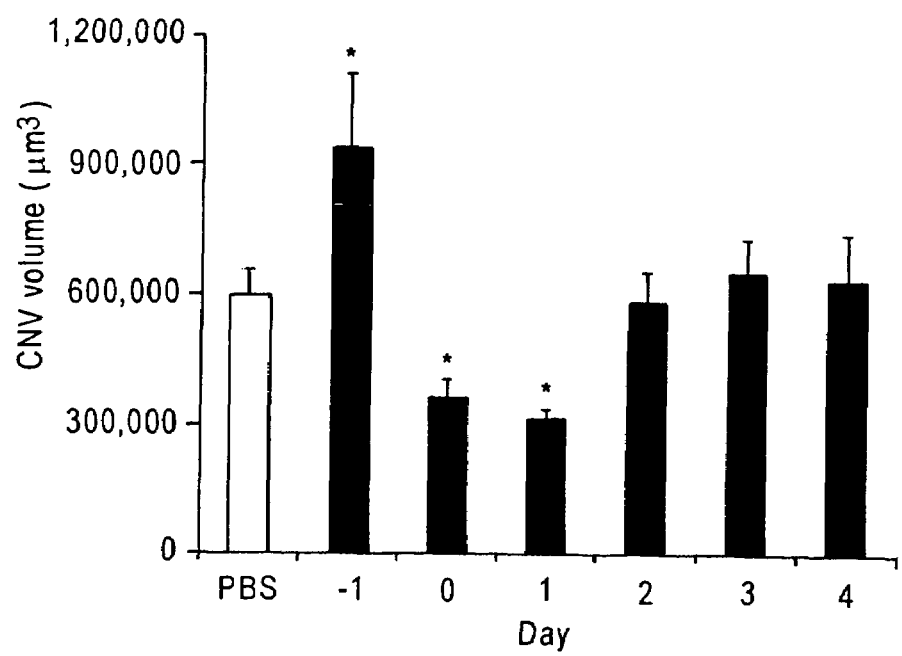
Figure 1K:
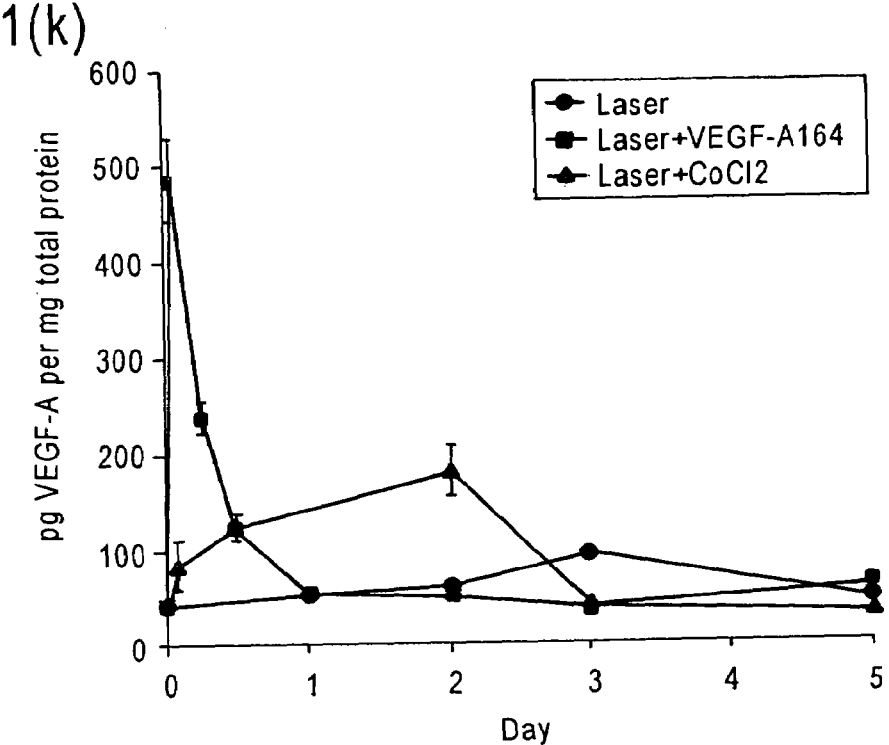
Figure 1L:
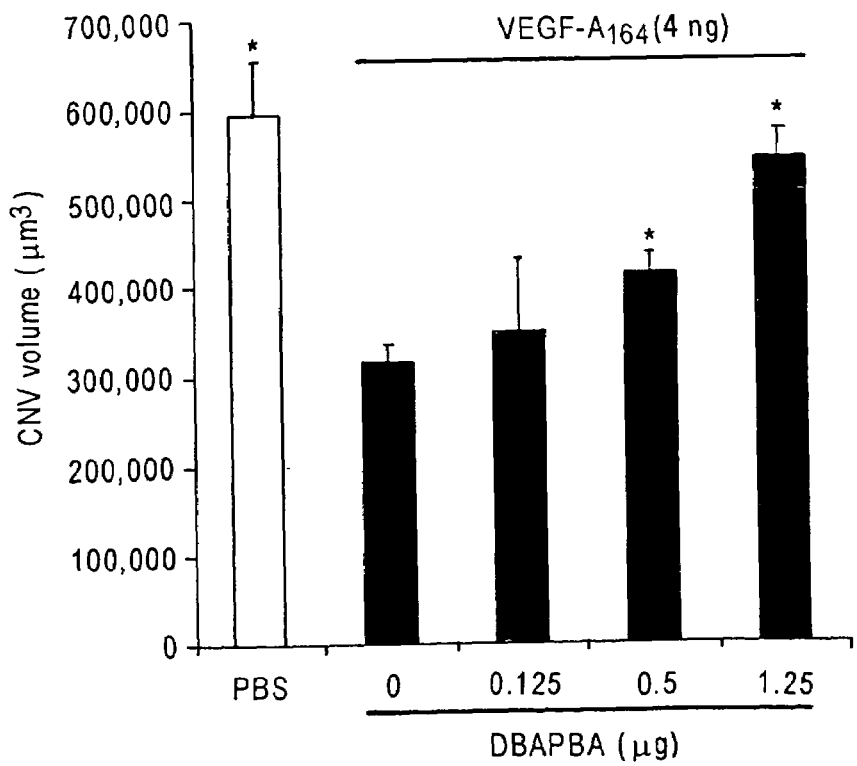

We found that a single intravitreous injection of VEGF-$A_{164}$ (4-12 ng), either immediately following or one day after laser injury, decreased peak Ccl-2 levels, the maximal number of choroidal macrophages, and volume of CNV both at 1 and 2 weeks following laser injury (FIG. 1a-d and FIG. 1i-j). Administration of VEGF-$A_{164}$ two or more days following laser injury, when macrophage infiltration already has occurred, did not reduce CNV (FIG. 1i-j). These data show that VEGF-A can evoke an anti-angiogenic response in this model of inflammatory neovascularization only when administered before macrophage recruitment, suggesting that it is through reduction of macrophage infiltration that this unusual action is mediated. Equimolar doses of basic fibroblast growth factor (FGF-2), another potent angiogenic cytokine, did not evoke similar responses (FIG. 1c), indicating that the anti-angiogenic effect is not a generic response to exogenous mitogenic proteins.

To test whether endogenous VEGF-A would induce similar effects, we injected $CoCl_2$ or $H_2O_2$, both of which upregulate VEGF-A expression. Intravitreous injection of either $CoCl_2$ (0.1 µg) or $H_2O_2$ (0.1 µg) one day after laser injury decreased the volume of CNV one week following laser injury, and was abrogated by neutralizing VEGF-A antibody (FIG. 1e). Although $CoCl_2$ or $H_2O_2$ can induce pleiotropic effects in cells, reversal of their anti-angiogenic effect by specific neutralization of VEGF-A confirms the involvement of this mechanistic pathway. Because hypoxia and reactive oxygen intermediates have been speculated to be involved in CNV (reviewed in Ambati, J., Ambati, B. K., Yoo, S. H., Ianchulev, S. & Adamis, A. P. *Age-related macular degeneration: etiology, pathogenesis, and therapeutic strategies.* (2003) Surv Ophthalmol 48, 257-293), the effects of $CoCl_2$ or $H_2O_2$ may have pathophysiological relevance.

Example 2

VEGF-A Levels are Pathophysiologically Relevant

The peak VEGF-A concentration in the RPE and choroid following VEGF-$A_{164}$ injection is 4-fold higher than its maximal level following laser injury alone, and rapidly declines to basal levels within one day (FIG. 1i,j). This peak level of 1.5±0.3 ng/ml is on the same order of magnitude as the VEGF-A concentration in the subretinal space, which is immediately adjacent to the RPE and choroid, of patients with retinal detachment or retinopathy of prematurity (ROP). Moromizato, Y., Hayashi, H., Kato, H., Ozaki, H. & Oshima, K. *Concentration of vascular endothelial growth factor within the subretinal space and vitreous fluid in rhegmatogenous retinal detachment.* (1997) Nippon Ganka Gakkai Zasshi 101, 498-502. Lashkari, K. et al. *Vascular endothelial growth factor and hepatocyte growth factor levels are differentially elevated in patients with advanced retinopathy of prematurity.* (2000) Am J Pathol 156, 1337-1344. $CoCl_2$ injection led to peak VEGF-A levels even less than after VEGF-$A_{164}$ injection, and less than double the maximal levels following laser injury alone (FIG. 1i,j), and is similar to intraocular levels in patients with diabetic retinopathy and plasma levels in patients with cancer. Over the first 3 days after injury, aggregate VEGF-A exposure (area under the curve) to the RPE and choroid following injection of VEGF-$A_{164}$ or $CoCl_2$ was only 49% or 52% higher, respectively, than after laser injury alone. These data show that our experimental conditions result in VEGF-A levels that are pathophysiologically relevant.

Example 3

VEGFR-1 Mediates Anti-Angiogenic Actions of VEGF-A

Because VEGF-$A_{164}$ binds not only VEGFR-1 and VEGFR-2 but also the neuropilin (NP) receptors, we tested the effects of placenta growth factor-1 (PlGF-1), a VEGFR-1 specific ligand (Park, J., Chen, H., Winer, J., Houck, K. & Ferrara, N. *Placenta growth factor. Potentiation of vascular endothelial growth factor bioactivity, in vitro and in vivo, and high affinity binding to Flt-1 but not to Flk-1/KDR.* (1994) J Biol Chem 269, 25646-25654), and VEGF-E, a VEGFR-2 specific ligand (Ogawa, S. et al. *A novel type of vascular endothelial growth factor, VEGF-E (NZ-7 VEGF), preferentially utilizes KDR/Flk-1 Receptor and carries a potent mitotic activity without heparin-binding domain.* (1998) J Biol Chem 273, 31273-31282), neither of which bind NP-1 or NP-2. A single intravitreous injection of PlGF-1 (40-1,250 ng) resulted in similar suppressive effects on macrophage recruitment and CNV whereas VEGF-E (4-12 ng) did not (FIG. 1c). We found that neutralizing antibody against VEGFR-1 (6 µg; $IC_{50}$=2-8 µg/ml) but not against VEGFR-2 (250 ng; $IC_{50}$=0.1-0.3 µg/ml) abolished the inhibition of CNV by VEGF-A, $CoCl_2$ or $H_2O_2$ (FIG. 1d,e and data not shown). The modest increase in CNV induced by VEGF-E was blocked by VEGFR-2 antibody but not VEGFR-1 antibody, confirming the specificity and effectiveness of these doses (FIG. 1f). CNV reduction induced by PlGF-1 was not enhanced by co-administration of VEGF-E, suggesting that cooperation between VEGFR-1 and VEGFR-2 is not required for anti-angiogenic activity (FIG. 1c). Although VEGF-E alone increased CNV volume, it was unable to overcome the anti-angiogenic effect of PlGF-1 of VEGF-A.

To demonstrate that the observed effects occurred through receptor binding triggered kinase activation through tyrosine phosphorylation, we used the following relatively selective small-molecule tyrosine kinase antagonists: SU5416 (3-((2,4-dimethylpyrrol-5-yl)methylidene]-indolin-2-one), which inhibits VEGFR-1 ($IC_{50}$=0.007-0.1 µM (Itokawa, T. et al. *Antiangiogenic effect by SU5416 is partly attributable to inhibition of Flt-1 receptor signaling*. (2002) Mol Cancer Ther 1, 295-302; Wood, J. M. et al. *PTK787/ZK 222584, a novel and potent inhibitor of vascular endothelial growth factor receptor tyrosine kinases, impairs vascular endothelial growth factor-induced responses and tumor growth after oral administration*. (2000) Cancer Res 60, 2178-2189); compared to VEGFR-2 ($IC_{50}$=1.0 µM (Itokawa, T. et al. (2002); Wood, et al. (2000); Fong, T. A. T. et al. *SU5416 is a potent and selective inhibitor of the vascular endothelial growth factor receptor (Flk-1/KDR) that inhibits tyrosine kinase catalysis, tumor vascularization, and growth of multiple tumor types*. (1999) Cancer Res 59, 99-106); and SU1498 ((E)-3-(3,5-diisopropyl-4-hydroxyphenyl)-2-[(3-phenyl-n-propyl)amino-carbonyl]acrylonitrile), which inhibits VEGFR-2 ($IC_{50}$=0.7 µM; Hennequin, L. F. et al. *Design and structure-activity relationship of a new class of potent VEGF receptor tyrosine kinase inhibitors*. (1999) J Med Chem 42, 5369-89; Rollin, S. et al. *VEGF-mediated endothelial P-selectin translocation: role of VEGF receptors and endogenous PAF synthesis*. (2004) Blood 103, 3789-3797) but not VEGR-1. (Rollin et al. (2004). We also used DBAPBA (3-2,5-dihydroxybenzylamino)phenylboronic acid), a recently described antagonist of VEGFR-1 kinase activity (IC50=40 µM. Asano, T., Nakamura, H., Uehara, Y. & Yamamoto, Y. *Design, synthesis, and biological evaluation of aminoboronic acids as growth-factor receptor inhibitors of EGFR and VEGFR-1 tyrosine kinases*. (2004) Chembiochem 5, 483-90. SU5416 (0.3 ng) and DBAPBA (1.5 µg), but not SU1498 (3.5 ng), blocked VEGF-A-induced suppression of Ccl-2, monocyte recruitment, and CNV (FIG. 1g and data not shown). The modest induction of CNV by VEGF-E was blocked by SU1498 but not SU5416 or DBAPBA, confirming the target receptor selectivity of these agents at these doses (FIG. 1g).

Although these findings are in line with the receptor neutralizing antibody data provide compelling evidence, we were mindful that SU5416 also can inhibit other kinases such as platelet derived growth factor receptor (PDGFR) (IC50=20 µM) (Itokawa, et al. (2002); Fong, et al, (1999)), flt3 (IC50=0.1-0.25 µM) (Yee, K. W. H. et al. *SU5416 and SU5614 inhibit kinase activity of wild-type and mutant FLT3 receptor tyrosine kinase*. (2002) Blood 100, 2941-2949), c-kit (IC50=0.1-1.0 µM) (Smolich, B. D. et al. *The antiangiogenic protein kinase inhibitors SU5416 and SU6668 inhibit the SCF receptor (c-kit) in a human myeloid leukemia cell line and in acute myeloid leukemia blasts*. (2001) Blood 97, 1413-1421), c-met (IC50=0.05 µM; ref). To control for these effects, we used AG1295 (6,7-dimethyl-2-phenylquinoxaline), which inhibits PDGFR (IC50=0.4 µM) (Kovalenko, M. et al. *Selective platelet-derived growth factor receptor kinase blockers reverse sis-transformation*. (1994) Cancer Res 54, 6106-14), flt3 (IC50=0.5 µM) (Levis, M., Tse, K.-F., Smith, B. D., Garrett, E. & Small, D. *A FLT3 tyrosine kinase inhibitor is selectively cytotoxic to acute myeloid leukemia blasts harboring FLT3 internal tandem duplication mutations*. (2001) Blood 98, 885-887), and c-kit (IC50=1.8 µM) (Kovalenko, et al. (1994)), and PHA665752, a potent inhibitor of c-met (IC50=0.05 µM) (Christensen, J. G. et al. *A selective small molecule inhibitor of c-Met kinase inhibits c-Met-dependent phenotypes in vitro and exhibits cytoreductive anti-tumor activity in vivo*. (2003) Cancer Res 63, 7345-55). Neither AG1295 (15 ng) nor PHA665752 (0.4 ng) blocked VEGF-A-induced CNV suppression.

Interestingly VEGFR-1 blockade by neutralizing antibody or SU5416 augmented the increase in CNV induced by VEGF-E (FIGS. 1f, g), suggesting that in the setting of exogenously triggered selective VEGFR-2 signaling, endogenous VEGFR-1 activation functions as a negative regulator of angiogenesis. Finally we studied the response of Vegfr-1 tk-/- mice to laser injury. Interestingly their CNV response was higher than that of wild-type mice, confirming that VEGFR-1 negatively modulates the angiogenic response (FIG. 1h). In addition, unlike in wild-type mice, exogenous VEGF-A164 (4 ng) did not decrease CNV in Vegfr-1 tk-/- mice. Collectively these data demonstrate that the in vivo suppressive effects of VEGF-A occur through active VEGFR-1 signaling and not by its functioning as a decoy receptor sequestering ligand from VEGFR-2.

At the time of VEGFR-1 antibody, SU5416, or DBAPBA administration one day after laser injury, macrophage recruitment has not yet occurred; thus, its action cannot be attributed to interference with VEGFR-1 receptors on macrophages. Although neutrophils expressing VEGFR-1 are recruited to the site of laser injury within 1 day, exogenous VEGF-$A_{164}$ (4 ng) injected one day after injury suppressed laser-induced CNV by 37±6%, even when neutrophils were depleted by anti-Gr-1 antibody treatment (P=0.36 compared with 47±4% CNV reduction by VEGF-A without neutrophil depletion). In addition, exogenous VEGF-$A_{164}$ (4 ng) injected immediately after injury, when neutrophils are not yet present, also inhibited CNV (FIG. 1i-j).

Figure 1M:
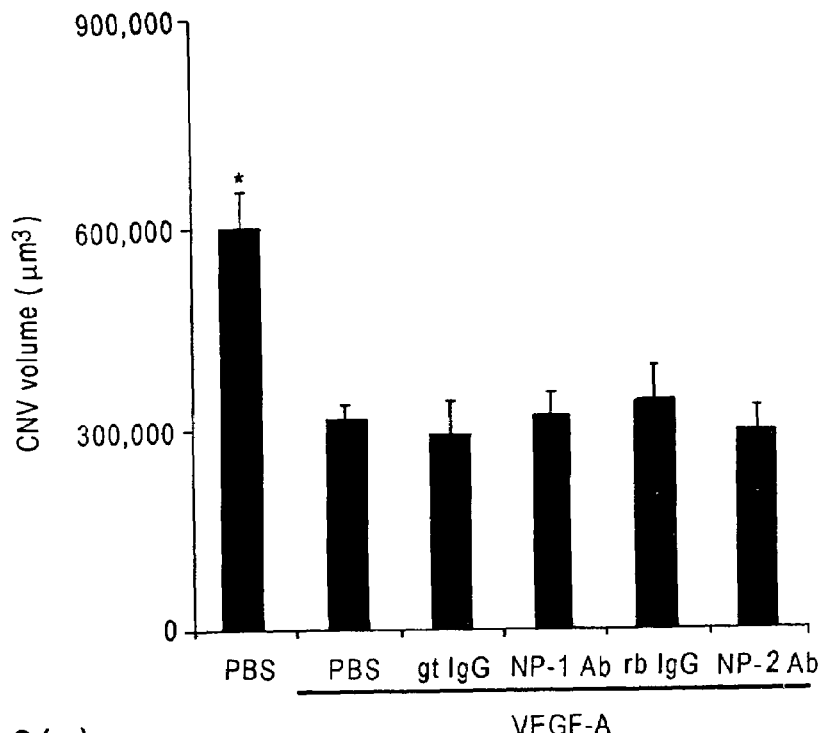

To further examine the potential role of the NPs, which are coreceptors for VEGFR-2, we studied other members of the VEGF/PlGF family. VEGF-$A_{120}$, which binds VEGFR-1 and VEGFR-2 but not the NPs, was as effective as, but less potent than, VEGF-$A_{164}$ in decreasing CNV (FIG. 1c), consistent with its lower binding affinity to VEGFR-1. Keyt, B. A. et al. *The carboxyl-terminal domain (111-165) of vascular endothelial growth factor is critical for its mitogenic potency*. (1996) J Biol Chem 271, 7788-95. PlGF-1, which also binds VEGFR-1 with much lower affinity than VEGF-$A_{164}$ (Park, J. et al. (1994)) was not only less potent but also slightly less effective, perhaps because of divergent agonist trafficking, as PlGF-1 and VEGF-$A_{164}$ differentially phosphorylate VEGFR-1. Autiero, M. et al. *Role of PlGF in the intra- and intermolecular cross talk between the VEGF receptors Flt1 and Flk1*. (2003) Nat Med 9, 936-43. PlGF-2, which binds VEGFR-1 as well as both NPs (Gluzman-Poltorak, Z., Cohen, T., Herzog, Y. & Neufeld, G. *Neuropilin-2 is a receptor for the vascular endothelial growth factor (VEGF)forms VEGF-145 and VEGF-165*. (2000) J. Biol. Chem. 275, 18040-18045), was similar to PlGF-1 in inhibiting CNV (FIG. 1c). VEGF-$A_{164}$ induced CNV inhibition was unaffected by neutralizing antibodies against NP-1 or NP-2 (FIG. 1m). Collectively these data strongly suggest that NPs do not modulate CNV suppression by VEGF-A.

Example 4

VEGFR-1 Negatively Transduces VEGFR-2 Signaling Via SHP-1

We studied whether VEGF-A executes its anti-angiogenic program by directly promoting VEGFR-1 activity or antagonizing VEGFR-2 activity. Constitutive cell surface expression of VEGFR-1 and VEGFR-2 on RPE cells in vivo were not significantly altered one day after laser injury, nor were they different at any time during the week after injury between eyes injected with VEGF-$A_{164}$ (on day 1) and those injected with PBS (FIG. 2a,b). There was however, a significant and monotonic decrease in VEGFR-1, but not VEGFR-2, expression on choroidal endothelial cells (CEC) during the week following laser injury, but there were no differences between VEGF-$A_{164}$- and PBS-injected eyes.

We found that the constitutive in vivo VEGFR-1/VEGFR-2 ratio, relatively quantitated by flow cytometry, on mouse CEC was 3.4±0.7 times higher (P=0.014) than on mouse retinal endothelial cells (REC), which is similar in this attribute to human umbilical vein endothelial cells, mouse lung or brain microvascular endothelial cells (Supplementary Figure). The significantly higher expression of VEGFR-1 on CEC, reflective of functional heterogeneity of endothelial cells in different microenvironments, may underlie the paradoxical effect of VEGF-A, routed through VEGFR-1, that we observed in the subretinal tissues.

VEGFR-1 tyrosine kinase phosphorylation was markedly enhanced following injection of VEGF-$A_{164}$ or PlGF-1 but not VEGF-E one day after laser injury. (FIG. 2c and data not shown). This inhibited VEGFR-2 phosphorylation by increasing the interaction between the protein tyrosine phosphatase (PTP) Src homology domain 2 (SH2)-containing tyrosine phosphatase-1 (SHP-1) and the VEGFR-2 complex (FIG. 2d and data not shown). We confirmed that VEGFR-2 dephosphorylation translated in to a functional inhibition of angiogenesis, because bis(maltolato)oxovanadium(IV) (BMOV), a pan-PTP inhibitor, abrogated VEGF-A-induced inhibition of CNV (FIG. 2e). VEGF-A-induced inhibition of CNV was abolished by sodium stibogluconate, a potent SHP-1 inhibitor (Pathak, M. K. & Yi, T. *Sodium stibogluconate is a potent inhibitor of protein tyrosine phosphatases and augments cytokine responses in hemopoietic cell lines.* (2001) J Immunol 167, 3391-7), but not by calpeptin, a specific inhibitor or the closely related SHP-2 (Schoenwaelder, S. M. et al. *The protein tyrosine phosphatase Shp-2 regulates RhoA activity.* (2000) Curr Biol 10, 1523-6) (FIG. 2e). Finally we demonstrated that SHP-$1^{-/-}$ mice were resistant to VEGF-A-induced CNV suppression (FIG. 2e). Collectively these data confirm a specific effect of exogenous VEGF-A on SHP-1. We also observed that VEGF-A did not modulate the interaction between VEGFR-2 and other PTPs such as PTP1B and human low molecular weight cytoplasmic PTP (HCPTPA) (data not shown). These data demonstrate that, following laser injury, excess VEGF-A negatively transduces VEGFR-2 signaling, unraveling a novel mechanism by which VEGF-A can modulate its own angiogenic actions.

Example 4

SPARC Silences VEGFR-1 Activation

Figure 3A:
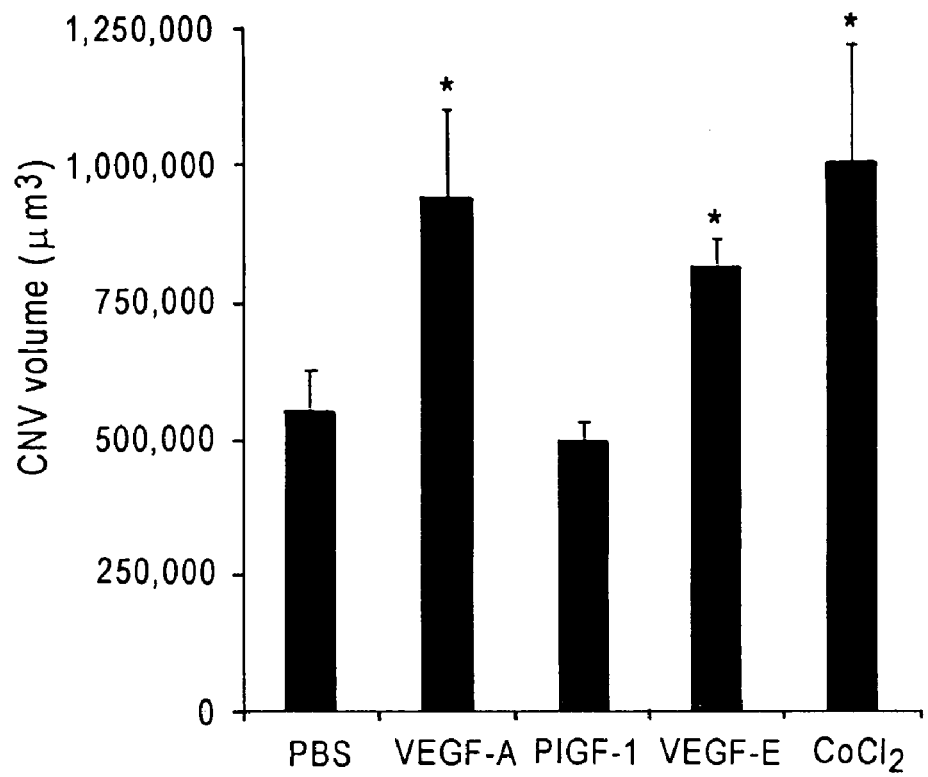

In contrast to its anti-angiogenic action when injected after laser injury, VEGF-$A_{164}$ increased CNV when injected one day before laser injury (FIGS. 1i-j). This was mediated via VEGFR-2 signaling because VEGF-E but not PlGF-1 promoted CNV when injected one day before injury (FIG. 3a). In addition, VEGFR-2 antibody but not VEFGR-1 antibody abolished this pro-angiogenic response). Whereas VEGF-$A_{164}$ enhanced tyrosine kinase phosphorylation of VEGFR-1 and decreased that of VEGFR-2 after injury, the opposite pattern of receptor tyrosine kinase phosphorylation emerged when VEGF-$A_{164}$ was injected before injury (data not shown). VEGF-$A_{164}$ also increased Ccl-2 secretion and macrophage recruitment when injected before injury (data not shown). In most tissues, VEGFR-1 autophosphorylation is weak, possibly because it is constitutively repressed. Therefore, we postulated the existence of a protein that restrains VEGFR-1 kinase at rest and is downregulated after injury, unsilencing its activation.

Figure 3B:
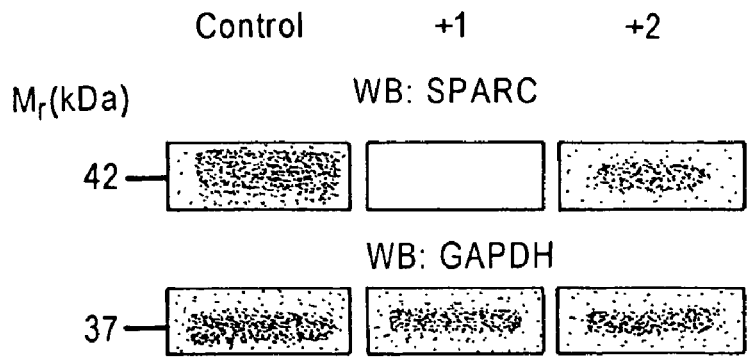
Figure 3C:
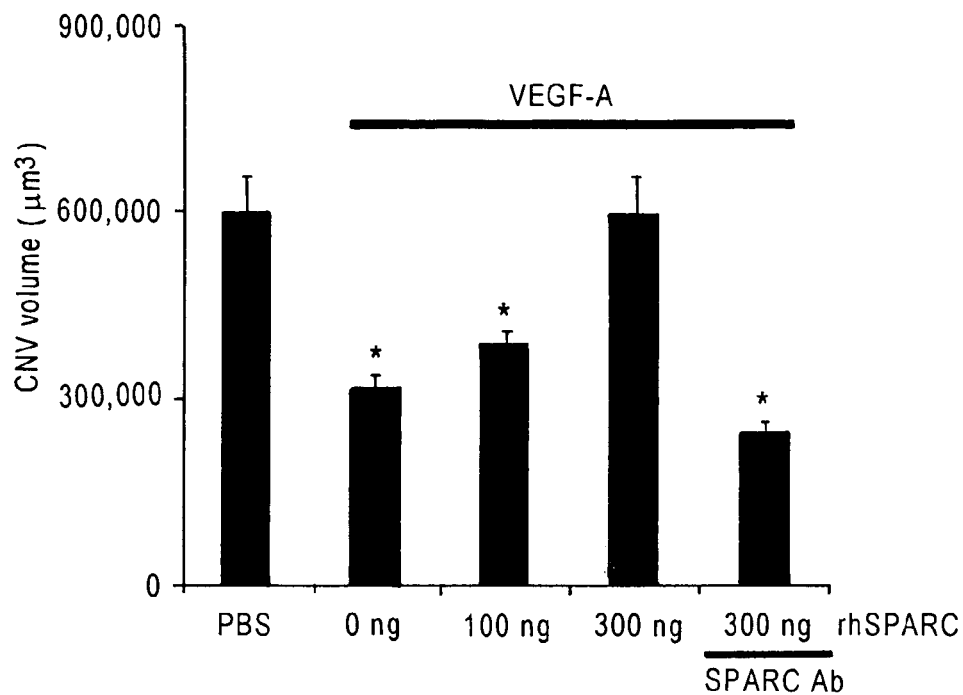
Figure 3D:
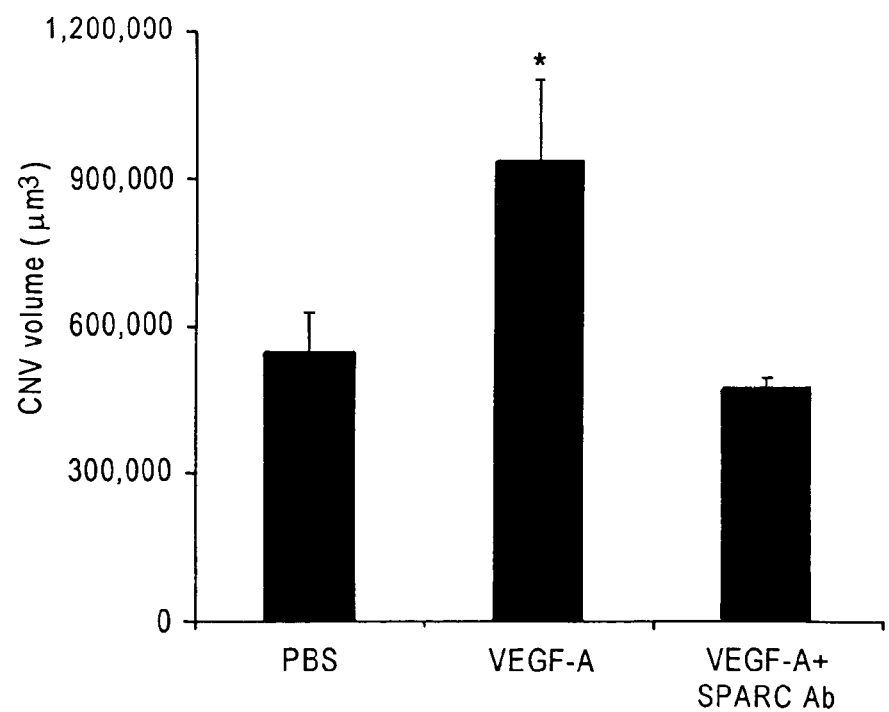
Figure 3E:
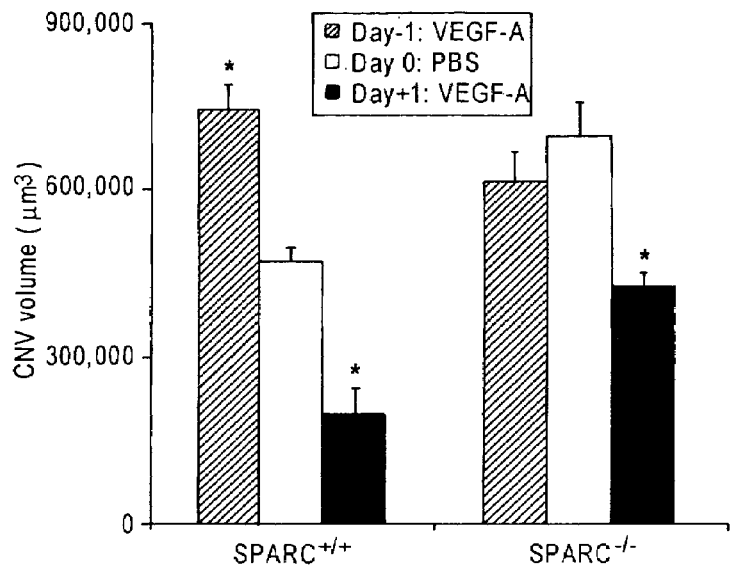
Figure 3F:
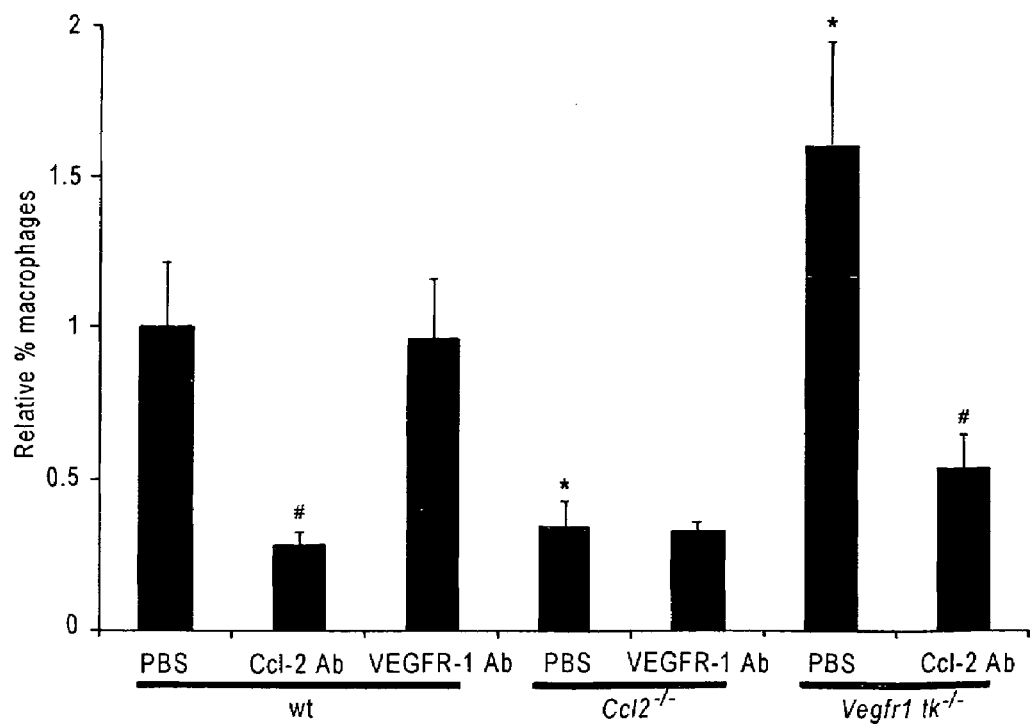

One such candidate is the matricellular protein SPARC, which inhibits the kinase activity of VEGFR-1 but not VEGFR-2 in vitro. Kupprion, C., Motamed, K. & Sage, E. H. *SPARC (BM-40, osteonectin) inhibits the mitogenic effect of vascular endothelial growth factor on microvascular endothelial cells.* (1998) J Biol Chem. 273, 29635-29640. We found that SPARC was constitutively expressed in the RPE and choroid, but that its expression declined within 6 hours after laser injury and was markedly downregulated one day after laser injury, recovering to near-baseline levels two days following injury (FIG. 3b). Suppression of CNV induced by VEGF-$A_{164}$ injected one day after injury, when SPARC levels are decreasing, was dose-dependently abolished by recombinant human SPARC (which has a high degree of identity to murine SPARC) (FIG. 3c). The restoration of CNV volume by exogenous SPARC was abolished by a neutralizing antibody to SPARC, confirming the specificity of this response. (FIG. 3c). Exogenous SPARC injection alone did not alter CNV (data not shown). We also found that neutralizing antibody to SPARC abolished increased CNV resulting from VEGF-$A_{164}$ injected one day before injury when SPARC is expressed in high amounts (FIG. 3d).

We found that the pro- and anti-angiogenic action of VEGF-$A_{164}$ injected before versus after injury, respectively, was duplicated in Sparc+/+ mice. However, in Sparc-/- mice, the pro-angiogenic response of VEGF-$A_{164}$ injected one day before injury was abolished, while the anti-angiogenic response of VEGF-$A_{164}$ injected one day after injury was preserved. We also made the interesting observation that the basal CNV response in Sparc-/- mice was significantly greater than in Sparc+/+ mice, consistent with the anti-angiogenic role described for endogenous SPARC in wound healing and tumor models. Chlenski, A. et al. *SPARC Is a key Schwannian-derived inhibitor controlling neuroblastoma tumor angiogenesis.* (2002) Cancer Res 62, 7357-7363; Brekken, R. A. et al. *Enhanced growth of tumors in SPARC null mice is associated with changes in the ECM.* (2003) J. Clin. Invest. 111, 487-495; Bradshaw, A. D., Reed, M. J. & Sage, E. H. *SPARC-null mice exhibit accelerated cutaneous wound closure. J. Histochem.* (2002) Cytochem. 50, 1-10. The modest difference between Sparc+/+ mice and C57BL/6J mice in basal CNV response may be attributed to the genetic variation arising from their mixed background. Collectively these data strongly suggest that SPARC restrains the ability of excess VEGF-$A_{164}$ to suppress CNV via VEGFR-1, and that the transient decline of SPARC in the wake of injury permits the anti-angiogenic action of VEGF-$A_{164}$ due to unsilencing of VEGFR-1 activation.

Example 5

Anti-Angiogenic Action of VEGF-A is Mediated Via Ccl-2 and Ccr-2

Figure 4A:
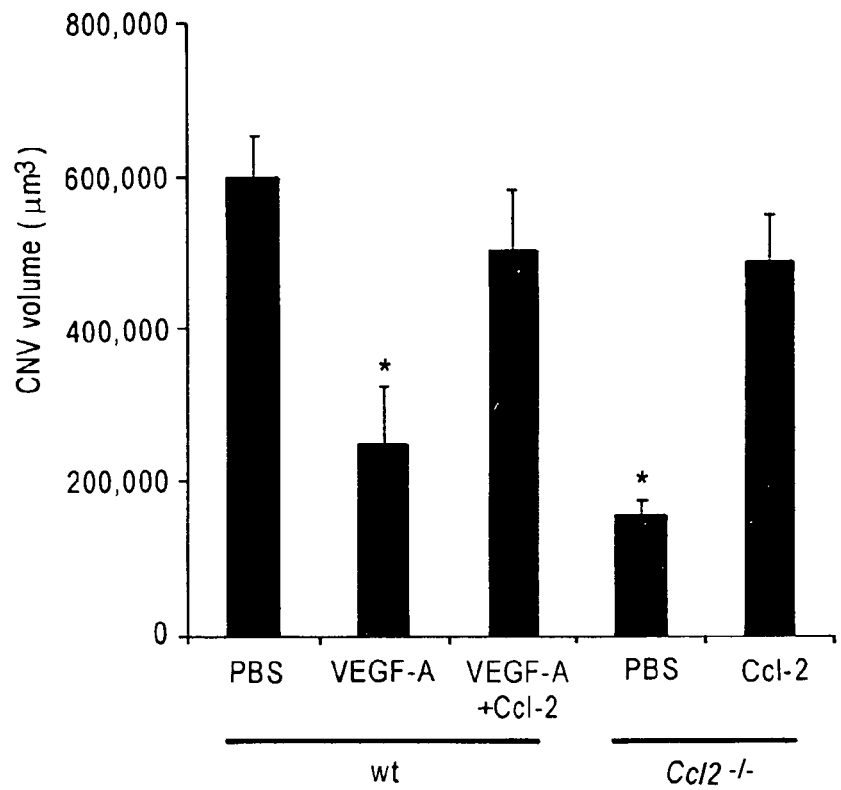
Figure 4B:
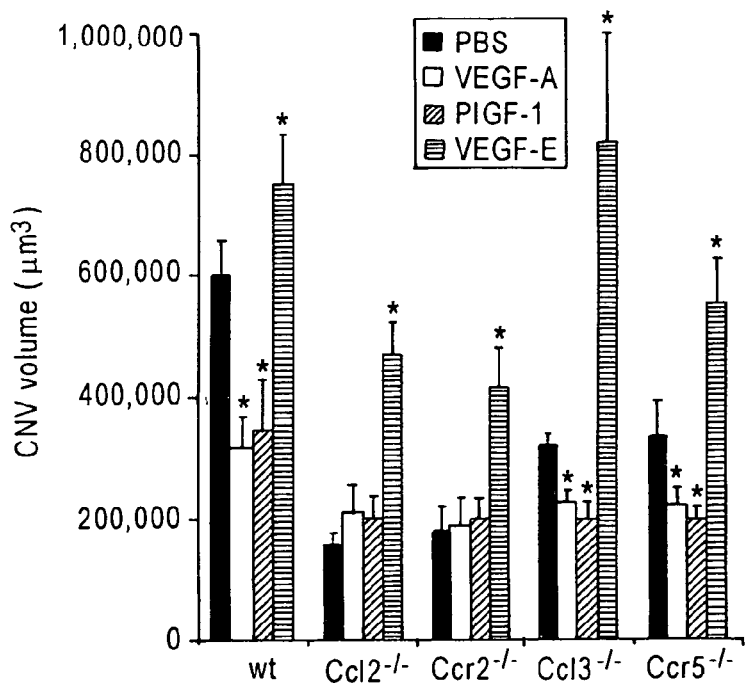

Reversing VEGF-$A_{164}$-induced deficiency of endogenous Ccl-2 by exogenous recombinant Ccl-2 abrogated VEGF-$A_{164}$-induced CNV suppression (FIG. 4a). Because macrophage recruitment is essential for the development of laser-induced CNV, we tested responses in mice deficient either in Ccl-2 or its cognate receptor Ccr-2. Laser-induced CNV was markedly inhibited both in Ccl2$^{-/-}$ and Ccr2$^{-/-}$ mice (FIG. 4b). Recombinant Ccl-2 restored CNV in Ccl2$^{-/-}$ mice to wild-type levels, demonstrating the functional specificity both of the recombinant protein and the knockout phenotype (FIG. 4a). Neither VEGF-$A_{164}$ nor PlGF-1 induced additional suppression of CNV in these knockout animals (FIG. 4b), consistent with the hypothesis that they inhibit angiogenesis principally via Ccl-2 suppression. Furthermore, CNV volumes in wild-type mice treated with the VEGF-$A_{164}$ or PlGF-1 were not significantly different from those in untreated Ccl2$^{-/-}$ or Ccr2$^{-/-}$ mice (P>0.20). VEGF-E administration in Ccl2$^{-/-}$ or Ccr2$^{-/-}$ mice restored CNV volumes nearly to wild-type levels (FIG. 4b), suggesting that unopposed VEGFR-2 activation can compensate for relative macrophage deficiency.

Figure 4C:
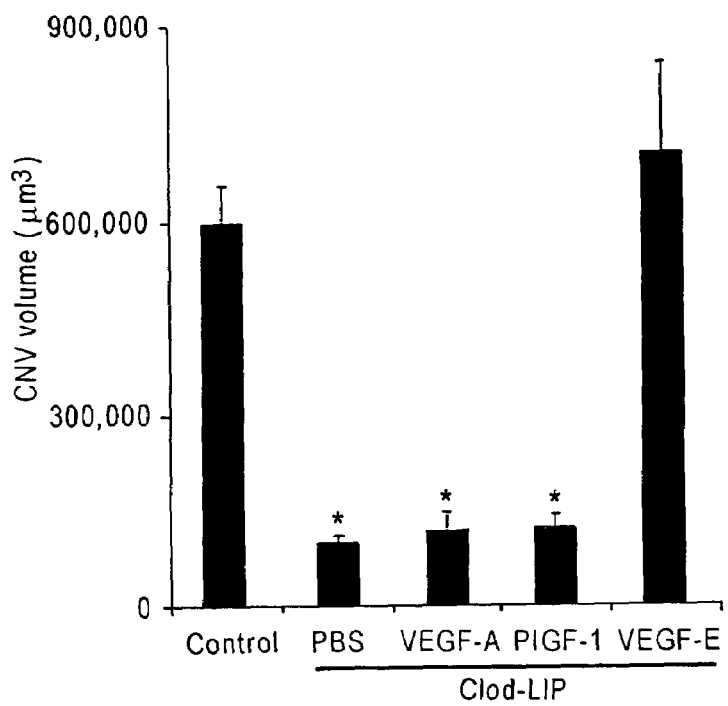

Although Ccl2$^{-/-}$ and Ccr2$^{-/-}$ mice are quite resistant to laser-induced CNV, greater abolition of laser-induced CNV is achieved by pharmacological depletion of macrophages induced by clodronate liposomes. Sakurai, E., Anand, A., Ambati, B. K., van Rooijen, N. & Ambati, J. *Macrophage depletion inhibits experimental choroidal neovascularization.* (2003) Invest Ophthalmol Vis Sci 44, 3578-85. While the Ccl-2-Ccr-2-axis is principally responsible for induced macrophage trafficking in vivo (Lu, B. et al. *Abnormalities in monocyte recruitment and cytokine expression in monocyte chemoattractant protein 1-deficient mice.* (1998) J Exp Med 187, 601-8; Kuziel, W. A. et al. *Severe reduction in leukocyte adhesion and monocyte extravasation in mice deficient in CC chemokine receptor 2.* (1997) Proc Natl Acad Sci USA 94, 12053-8), we found that laser injury also stimulates expression of the minor monocyte chemoattractant Ccl-3 (data not shown). This may explain the moderate degree of choroidal macrophage recruitment after laser injury in Ccl2$^{-/-}$ or Ccr2$^{-/-}$ mice, and the incomplete suppression of CNV in these mice as compared to clodronate liposome-treated animals (FIG. 4c). Laser-induced CNV is inhibited in mice deficient in Ccl-3 or its receptor Ccr-5 to a lesser degree than in Ccl2$^{-/-}$ or Ccr2$^{-/-}$ mice (FIG. 4b), indicating that the Ccl-3-Ccr-5-axis plays a minor role in this injury response.

The inability of VEGF-$A_{164}$ and PlGF-1 to completely suppress monocyte recruitment and CNV may result in part from the redundancy afforded by the Ccl-3-Ccr-5 axis, as neither VEGF-$A_{164}$ nor PlGF-1 affected Ccl-3 production by CEC or RPE cells, which was approximately 4-fold lower than Ccl-2 production (data not shown). While Ccl3$^{-/-}$ and Ccr5$^{-/-}$ mice had mildly attenuated CNV responses to laser injury, both VEGF-$A_{164}$ and PlGF-1 were able to further suppress CNV in these mice to the levels in untreated Ccl2$^{-/-}$ or Ccr2$^{-/-}$ mice and in VEGF-$A_{164}$ or PlGF-1-treated wild-type mice (FIG. 4b). Although Ccl-2 and Ccr-5 can recruit T-lymphocytes and NK-cells (Ruffing, N., Sullivan, N., Sharmeen, L., Sodroski, J. & Wu, L. *CCR5 has an expanded ligand-binding repertoire and is the primary receptor used by MCP-2 on activated T cells.* Cell (1998) Immunol 189, 160-8), neither of these cell types are recruited to the eye in significant numbers following laser injury (data not shown). We also found that laser-induced CNV was unaffected by systemic depletion of CD4+, CD8+, or NK cells.

Neither VEGF-A nor PlGF-1 induced additional suppression of CNV in clodronate liposome-treated animals (FIG. 4c), consistent with the hypothesis that they inhibit angiogenesis principally via Ccl-2 suppression and subsequent macrophage recruitment. VEGF-E administration in clodronate liposome-treated mice restored CNV volumes nearly to wild-type levels (FIG. 4c), again suggesting that unopposed VEGFR-2 activation of CEC can promote angiogenesis even in the absence of macrophages.

Example 6

Exogenous VEGF-A Reduces Vasculogenesis

Figure 4D:
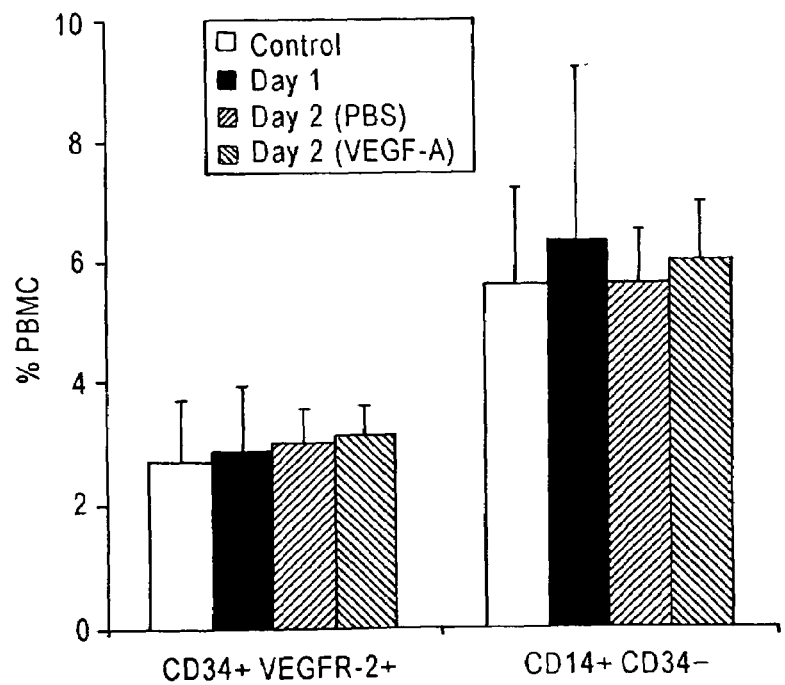

Laser-induced CNV forms both via angiogenesis and vasculogenesis, although only a minor fraction of endothelial cells in CNV are bone marrow-derived. Takahashi, H. et al. *Contribution of bone-marrow-derived cells to choroidal neovascularization.* (2004) Biochemical and Biophysical Research Communications 320, 372-375. The precise origin and phenotypic characterization of endothelial progenitor cells (EPCs) continues to stir debate, especially because of recent findings that monocyte-lineage cells can assume an endothelial phenotype in neovasculature. We used flow cytometry to detect the fraction of peripheral blood mononuclear cells that were CD34$^+$VEGFR-2$^+$ or CD14$^+$CD34$^-$, populations that contain EPCs. Neither laser injury nor VEGF-$A_{164}$ (4 ng) injection one day after injury induced EPC mobilization into the peripheral blood (FIG. 4d). This is not surprising because EPC mobilization typically is observed after substantial injuries such as hindlimb ischemia, and doses of systemic VEGF-A (10-500 µg) required to mobilize EPCs far exceed that used here.

We tested the effect of VEGF-$A_{164}$ injection one day after laser injury in GFP chimeric mice 8 weeks following bone marrow transplantation in mice with engraftment exceeding 90%. In the RPE/choroid, GFP$^+$ cells were identified only at the site of laser injury and the immediate vicinity (data not shown). The bulk (>60%) of GFP$^+$ cells in the RPE/choroid following injury expressed either CD11b or F4/80, markers of monocytic lineage, while nearly all (>95%) CD11b$^+$ and F4/80$^+$ cells expressed GFP. Flow cytometry showed that 7 days after injury the number of GFP$^+$CD31$^+$ cells was 54.7±10.5% less in VEGF-$A_{164}$-(4 ng) treated eyes than in PBS-treated eyes (P=0.014; n=8). The vast majority (>90%) of GFP$^+$CD31$^+$ cells, both in PBS- and VEGF-$A_{164}$-treated eyes, also expressed CD11b or F4/80. These data reflect the well-known CD31 phenotypic overlap between endothelial cells and monocyte-lineage cells, and led us to define bone marrow derived endothelial cells (BMDECs) by their GFP$^+$CD31$^+$CD11b$^-$F4/80$^-$ phenotype.

Figure 4E:
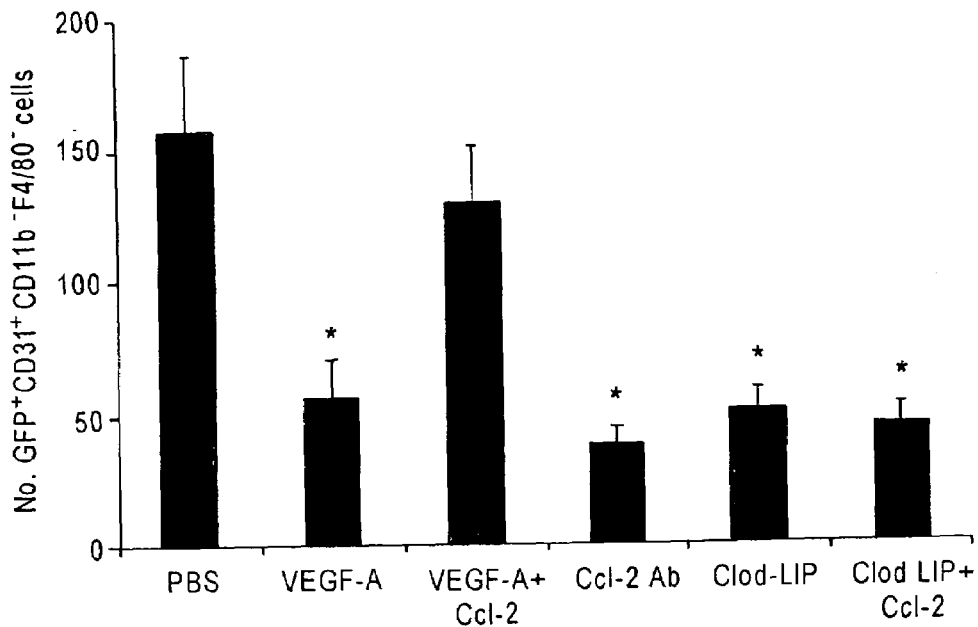

The number of BMDECs, seven days after injury, was significantly less in VEGF-$A_{164}$-(4 ng) treated eyes than in PBS-treated eyes (FIG. 4e). Reduction in vasculogenesis by VEGF-$A_{164}$ paralleled the decreased in total CNV volume (FIG. 1c), and was abrogated by recombinant Ccl-2 (0.55 ng), suggesting that VEGF-A-induced Ccl-2 suppression was responsible for the decline in BMDEC incorporation. In support of this notion, intercepting macrophage recruitment by Ccl-2 neutralizing antibody (1 ng) or depleting macrophages by clodronate liposomes both markedly reduced BMDEC incorporation. Recombinant Ccl-2 (0.55 ng) did not abrogate the effect of clodronate liposomes, demonstrating that the restorative effect of Ccl-2 is due to increased macrophage recruitment. These data support the growing body of evidence that bone marrow-derived monocyte-lineage cells can promote vasculogenesis by facilitating BMDEC incorporation through intercellular crosstalk or directly by differentiating into an endothelial cell type. While our findings do not distinguish between an instructive and plastic role, they reveal the necessity of Ccl-2-driven macrophage recruitment in promoting vasculogenesis in this model.

Figure 4F:
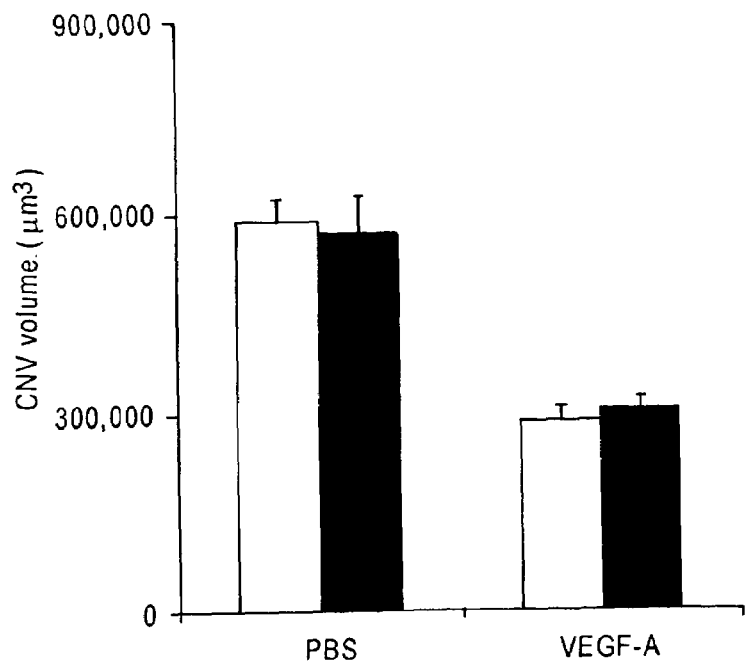

We found that the volume of CNV in eyes treated with PBS or VEGF-$A_{164}$ did not depend on whether the fellow eye was treated with PBS or VEGF-$A_{164}$, consistent with the independence of BMDEC incorporation from EPC mobilization, suggesting that the local microenvironment was more important in determining the total neovascular response than systemic factors (FIG. 4f).

Example 7

HO-1 Mediates Anti-Angiogenic Actions of VEGF-A

Figure 5A:
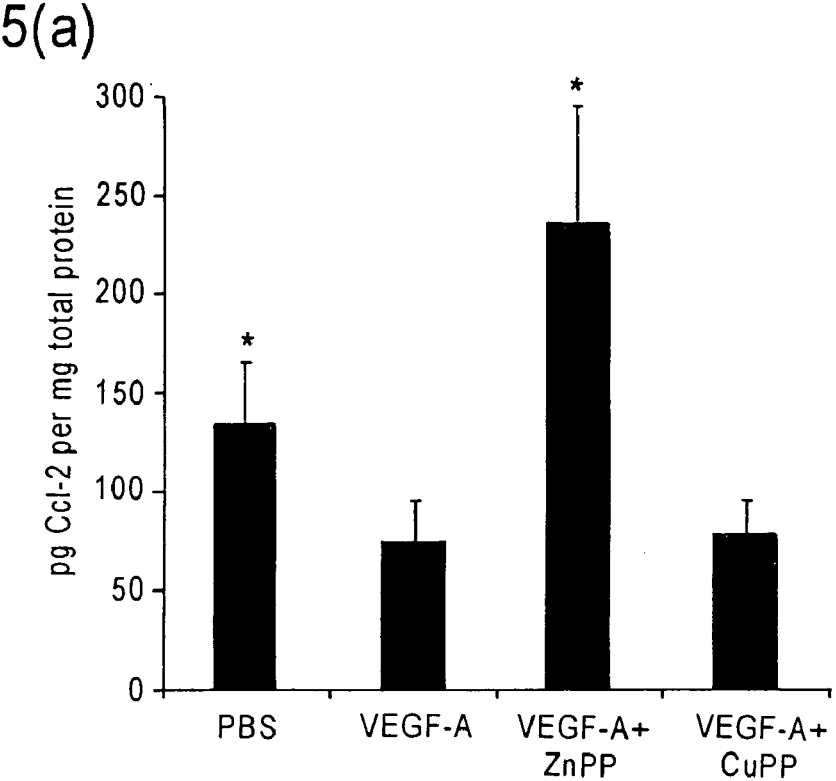
Figure 5B:
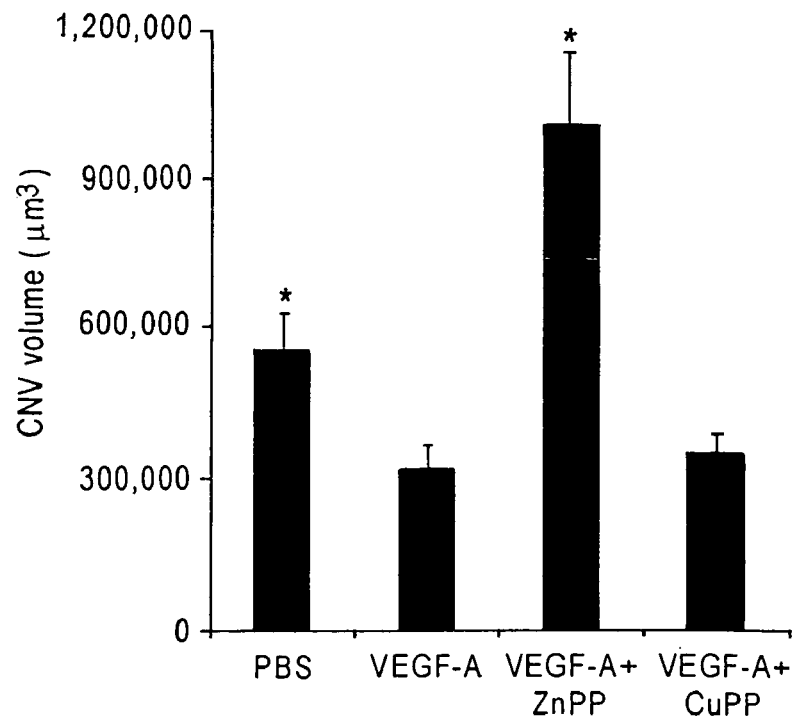
Figure 5C:
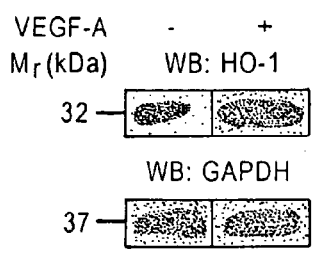
Figure 5D:
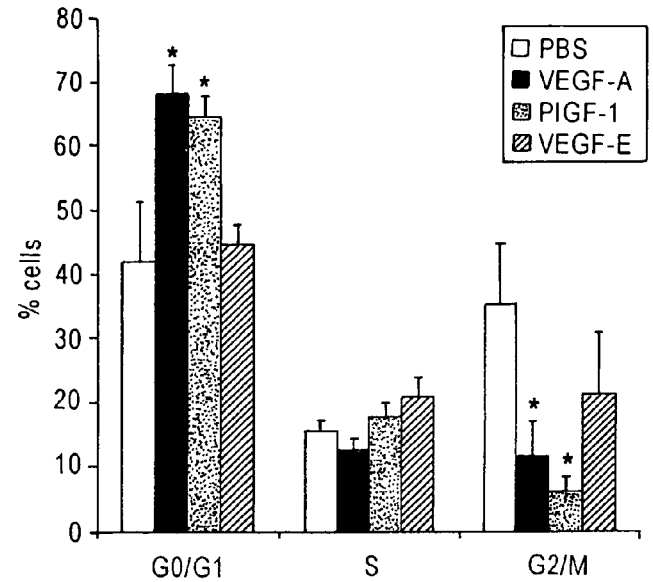

We queried the signaling pathways downstream from VEGFR-1 potentially responsible for mediating its anti-angiogenic and anti-inflammatory functions by examining potential candidate molecules. We observed that laser injury induced HO-1, and that VEGF-$A_{164}$ (4 ng) augmented the expression of this potent anti-inflammatory heat shock protein (FIG. 5a). The HO-1 antagonist zinc protoporphyrin IX (ZnPP), but not copper protoporphyrin IX (CuPP), abolished the anti-inflammatory and anti-angiogenic effects of VEGF-A (FIG. 5b,c). HO-1 blockade increased CNV volumes to levels higher than control, suggesting that the moderate induction of HO-1 by laser injury itself modulates the basal angiogenic response (FIG. 5c).

We also examined whether the endogenous anti-angiogenic molecules pigment epithelium derived factor (PEDF) and soluble VEGFR-1, both of which are upregulated by VEGF-A in vitro (Ohno-Matsui, K., Yoshida, T., Uetama, T., Mochizuki, M. & Morita, I. *Vascular endothelial growth factor upregulates pigment epithelium-derived factor expression via VEGFR-1 in human retinal pigment epithelial cells.* (2003) Biochem Biophys Res Commun 303, 962-7; Barleon, B. et al. *Vascular endothelial growth factor up-regulates its receptor fms-like tyrosine kinase 1 (FLT-1) and a soluble variant of FLT-1 in human vascular endothelial cells.* (1997) Cancer Res 57, 5421-5) and have been reported to inhibit laser-induced CNV (Mori, K. et al. *Pigment epithelium-derived factor inhibits retinal and choroidal neovascularization.* (2001) J Cell Physiol 188, 253-63; Honda, M., Sakamoto, T., Ishibashi, T., Inomata, H. & Ueno, H. *Experimental subretinal neovascularization is inhibited by adenovirus-mediated soluble VEGF/flt-1 receptor gene transfection: a role of VEGF and possible treatment for SRN in age-related macular degeneration.* (2000) Gene Ther 7, 978-85), are responsible for the reduction in CNV following VEGF-A administration. Expression of PEDF protein was unchanged while that of soluble VEGFR-1 was slightly decreased by exogenous VEGF-A injection following laser injury (FIG. 2f-g). VEGFR-1 can limit VEGFR-2-mediated human umbilical vein endothelial cell proliferation via nitric oxide (NO) (Bussolati, B. et al. (2001)); however, $N^\omega$-nitro-L-arginine methyl ester (L-NAME), an inhibitor of NO synthase, did not reverse VEGF-A-induced CNV suppression (FIG. 2f-g). Although these data exclude PEDF, soluble VEGFR-1, and NO, we cannot discount the potential involvement of other endogenous anti-angiogenic molecules.

Example 8

VEGF-A Induces $G_0/G_1$ Arrest of CEC

Figure 5E:
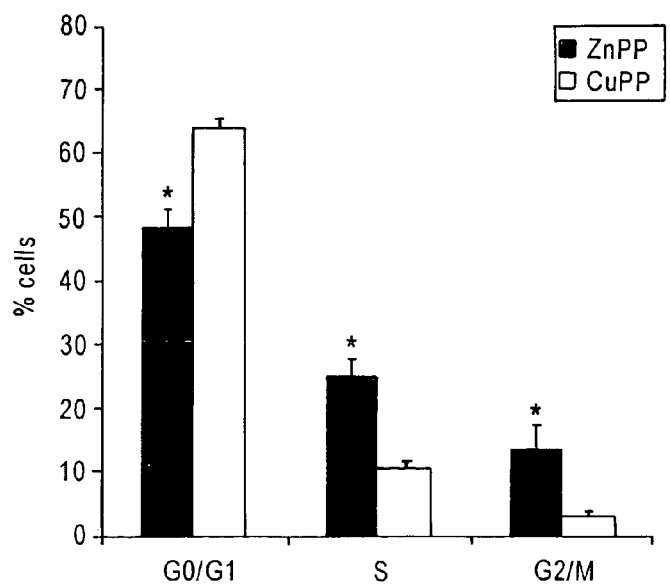
Figure 5F:
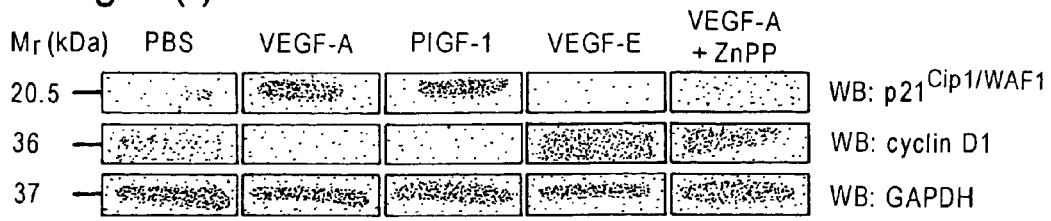

Apart from its anti-inflammatory effect, exogenous VEGF-$A_{164}$ directly inhibited the proliferation of choroidal endothelial cells (CEC) induced by laser injury, consistent with decreased CNV, but not by causing cell death. Rather, VEGF-$A_{164}$ and PlGF-1 induced accumulation of CEC in $G_0/G_1$ phases (FIG. 5d), which was reversed by inhibiting HO-1 using ZnPP (FIG. 5e). Cell cycle analysis showed no difference in the subdiploid (apoptotic) population in eyes injected with PBS compared with VEGF-$A_{164}$ (P=0.45) or PlGF-1 (P=0.23). Histology confirmed the absence of retinal or subretinal toxicity following VEGF-$A_{164}$ or PlGF-1 injection (data not shown). The abrogation of VEGF-A's anti-angiogenic effect by VEGFR-1 antagonists or HO-1 blockade also confirms the absence of an effect on endothelial cell viability. $G_0/G_1$ arrest induced by VEGF-$A_{164}$ and PlGF-1 was associated with upregulation of $p21^{Cip1/WAF1}$ and downregulation of cyclin D1, which were sensitive to HO-1 inhibition (FIG. 5f). VEGF-$A_{164}$ did not modulate $p27^{Kip1}$ levels (data not shown).

Example 9

Laser-Induced VEGF-A Promotes CNV Via Ccl-2

Blockade of VEGF-A by a variety of strategies has been reported to inhibit laser induced CNV. Saishin, Y. et al. *VEGF-TRAPR1R2 suppresses choroidal neovascularization and VEGF-induced breakdown of the blood-retinal barrier.* (2003) J Cell Physiol 195, 241-8. However, in most of these studies, the antagonists, while potent, were not selective for VEGF-A alone. In addition, these studies employed continual inhibition of VEGF-A for the entire duration of the wound healing response. We studied the effects of VEGF-A blockade, using a neutralizing antibody specific for mouse VEGF-A, during various stages of this injury model. Injected on days 0 and 1, neutralizing VEGF-A antibody (1 ng) significantly reduced CNV (55±13%; P=0.04) compared to control IgG. However, when injected on days 2 and 3, the inhibition was modest and insignificant (33±8%; P=0.07). When injected on days 4 and 5, the inhibitory effect was lost (7±19%; P=0.79). Because CNV was inhibited by VEGF-A neutralization only before macrophage recruitment, and closely paralleled decreased macrophage recruitment ($r^2$=0.8; P=0.03), we suspected that VEGF-A blockade interrupted the Ccl-2 pathway. Indeed we found that VEGF-A Ab, injected on days 0 and 1, decreased laser-induced peak Ccl-2 protein in the RPE and choroid by 37±12% (P=0.05). Injected on days 0 and 1, neutralizing VEGFR-2 antibody (125 ng) significantly decreased Ccl-2 by 45±12% (P=0.02) but neutralizing VEGFR-1 antibody (3 µg) did not (14±18%; P=0.42), indicating that endogenous VEGF-A induced Ccl-2 via VEGFR-2. Similarly, neutralizing antibody against VEGFR-2 but not VEGFR-1 inhibited CNV (data not shown). Recombinant Ccl-2 (0.55 ng) restored the CNV inhibited by VEGF-A antibody, confirming that downstream suppression of Ccl-2 is the proximate cause of the anti-angiogenic activity of VEGF-A neutralization. CNV reduction in wild-type mice treated with Ccl-2 antibody (77±4%) and in PBS-treated $Ccl2^{-/-}$ mice (74±3%), both outstripped CNV inhibition by VEGF-A antibody in wild-type mice (P<0.05), consistent with the incomplete suppression of Ccl-2 by VEGF-A antibody. Collectively these data suggest that the level of VEGF-A induced by laser injury supports angiogenesis indirectly via stimulation of Ccl-2 rather than by directly recruiting macrophages.

We compared the relative importance of Ccl-2 versus VEGFR-1 in macrophage recruitment and CNV following laser injury using neutralizing antibodies and $Ccl2^{-/-}$ and $Vegfr1\ tk^{-/-}$ mice. Neutralization of Ccl-2 in wild-type mice significantly inhibited macrophage recruitment to the same extent as in $Ccl2^{-/-}$ mice (Supplementary FIG. 3). VEGFR-1 neutralization did not inhibit macrophage recruitment in wild-type mice or further suppress it in $Ccl2^{-/-}$ mice. Macrophage recruitment, which was augmented in $Vegfr1\ tk^{-/-}$ mice consistent with their increased CNV, was reduced by Ccl-2 antibody. Collectively these data demonstrate that laser-induced macrophage recruitment relies principally on Ccl-2 and not VEGFR-1, and is consistent with the much higher peak Ccl-2 concentration (1.04±0.14 ng/ml, n=8) in the RPE/choroid, following laser injury, compared to VEGF-A (0.30±0.02 ng/ml, n=12, P<0.01).

Despite the existence of many chemokines, including VEGF-A and PlGF-1, that attract monocytes in vitro, Ccl-2 and Ccr-2 are uniquely essential for monocyte recruitment and induced macrophage trafficking in several inflammatory models in vivo. Daly, C. & Rollins, B. J. *Monocyte chemoattractant protein-1 (CCL2) in inflammatory disease and adaptive immunity: therapeutic opportunities and controversies.* (2003) Microcirculation 10, 247-57. The reduction of macrophage recruitment and subsequent CNV in Ccl2$^{-/-}$ and Ccr2$^{-/-}$ mice, despite normal expression of VEGF-A and PlGF-1 (data not shown), further supports the contention that the Ccl-2-Ccr-2 is the dominant axis of macrophage recruitment following laser injury.

Example 10

Biphasic Effect of VEGF-A

To further examine the question that excess VEGF-A, whether exogenously applied or endogenously induced before macrophage recruitment (days 0 or 1), decreases CNV, we tested the dose-ranging effect of recombinant human VEGF-A$_{165}$ (4 pg-4 ng) in the presence of neutralizing mouse VEGF-A antibody to eliminate the contribution of endogenous VEGF-A. We found that low-doses of VEGF-A$_{165}$ (4-400 pg) restored CNV inhibited by neutralization of endogenous VEGF-A, while high-doses (1-4 ng) reduced CNV back to the basal level observed in the presence of mouse VEGF-A antibody alone. This novel bidirectional dose-dependent effect of VEGF-A is anti-parallel to the recently described biphasic behavior of pigment epithelium derived factor (PEDF) (Apte, R. S., Barreiro, R. A., Duh, E., Volpert, O. & Ferguson, T. A. *Stimulation of neovascularization by the anti-angiogenic factor PEDF.* (2004) Invest Ophthalmol Vis Sci In press), although we did not observe modulation of PEDF in our system by VEGF-A.

Example 11

Zone of Inhibition

These data may be relevant to the well known but poorly understood clinical observation that often there is a single focus of CNV in patients with AMD despite widespread disease in the RPE and choroid (personal communication, N. M. Bressler and W. F. Mieler). Even when multiple foci exist, typically the ingrowth channels of CNV through Bruch membrane are separated by 1 to 2 mm, with several intervening fractures in Bruch membrane not containing CNV (personal communication, H. E. Grossniklaus and G. A. Lutty). Interestingly, therapeutic destruction of CNV nearly always results in recurrence in the immediate vicinity. We speculated that these phenomena results from high levels of VEGF-A emanating from the existing focus of CNV, creating a "zone of inhibition" that suppresses formation of adjacent CNV.

Figure 6B:
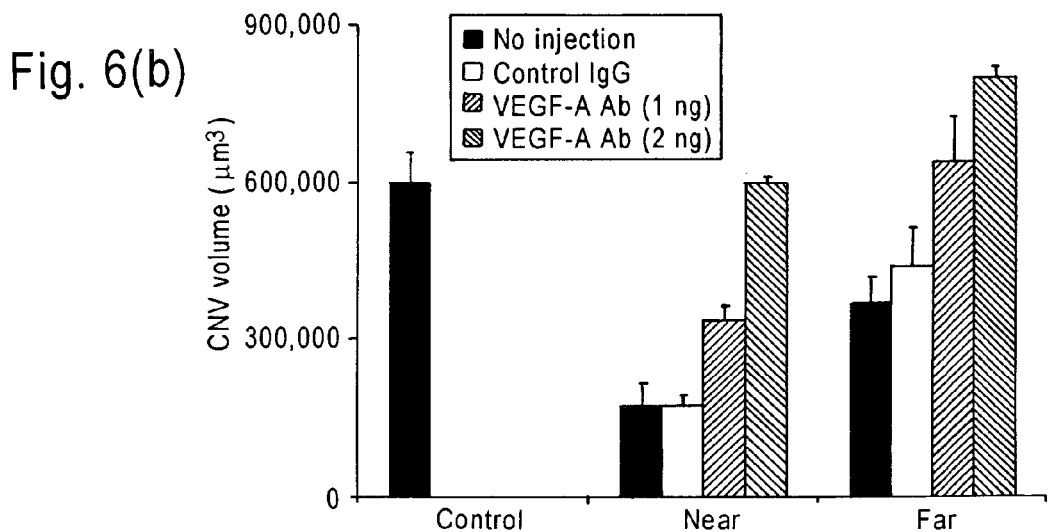
Figure 6C:
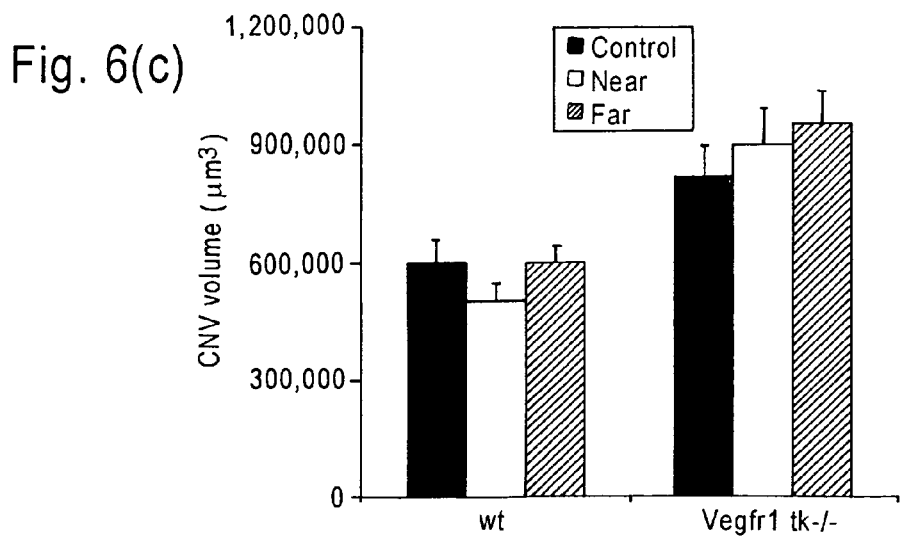

We tested whether a similar "zone of inhibition" existed in the mouse by placing laser burns at varying distances from an area of preexisting laser injury placed two days earlier. CNV volume was significantly inhibited in laser spots closer to (602±74 µm), but not in those further from (958±115 µm), the preexisting injury site (FIG. 6b). We also found that VEGF-A expression in response to the preexisting laser injury was responsible, at least in part, for the inhibition of CNV in the adjacent laser spot, because neutralizing VEGF-A antibody abolished this zone of inhibition. A lower dose of VEGF-A antibody (1 ng) was required to restore normal CNV volume in the more distant laser spots, while a great amount (2 ng) was required for the spots closer to the preexisting injury. This is consistent with the notion that diffusion of VEGF-A from the original injury suppresses CNV in the subsequent lesions. When laser spots were placed 10 days after initial injury there was no CNV inhibition, consistent with the absence of excess VEGF-A (FIG. 6c). In addition, we found that there was no suppression of subsequent CNV in Vegfr-1 tk$^{-/-}$ mice, indicating that the anti-angiogenic effect of endogenous VEGF-A is mediated via VEGFR-1. These novel data not only provide a mechanistic basis for the clinical observations, but also may provide insight both into why anti-VEGF-A therapies do not maintain the short-term success they exhibit in patients with CNV, and why they exhibit an inverse dose-response curve (http://www.fda.gov/ohrms/dockets/ac/04/briefing/2004-4053B1_02_FDA-Backgrounder.pdf).

Example 12

Excess VEGF-A Decreases Corneal Hemangiogenesis

To determine whether the anti-angiogenic effect of VEGF-A existed in other systems, we studied a clinically relevant model of corneal neovascularization induced by chemical and mechanical trauma. Ambati, B. K. et al. *Sustained inhibition of corneal neovascularization by genetic ablation of CCR5.* (2003) Invest Ophthalmol Vis Sci 44, 590-3; Ambati, B. K., Joussen, A. M., Kuziel, W. A., Adamis, A. P. & Ambati, J. *Inhibition of corneal neovascularization by genetic ablation of CCR2.* (2003) Cornea 22, 465-7. Although both belong to the eye, the cornea is extremely different from the choroid. Whereas the choroid has the highest blood flow of any tissue in the body, the cornea normally is avascular, one of only a few such tissues in the adult organism. Recent work has highlighted the importance of lymphangiogenesis in addition to hemangiogenesis in models of corneal injury.

Paralleling the contrasting effects of exogenous VEGF-A in CNV, we found that VEGF-A$_{164}$ injection (1 ng) increased corneal macrophage infiltration and hemangiogenesis (CD31$^+$LYVE-1$^-$ blood vessels) when injected one day before injury, and decreased them when injected immediately after injury (FIG. 7). As in the case of CNV, SPARC levels transiently decreased for (1 day) in the cornea (FIG. 7). Similar to the choroid, we found an exaggerated expression of VEGFR-1 receptors on conjunctival endothelial cells. We found that the constitutive in vivo VEGFR-1/VEGFR-2 ratio, relatively quantitated by flow cytometry, on mouse conjunctival endothelial cells was 3.4±0.7 times higher (P=0.02) than on mouse retinal endothelial cells (REC).

Interestingly, we found that VEGF-A$_{164}$ (1 ng) injected one day before injury increased lymphangiogenesis (LYVE-1$^+$ lymphatic vessels) but did not decrease it when injected immediately after injury. The immunity of the lymphatic vasculature to the anti-angiogenic effect of VEGF-A may stem from its lack of VEGFR-1 expression, which we confirmed in the cornea (data not shown). Parenthetically, we did not observe LYVE-1$^+$ vessels in laser-induced CNV (data not shown).

Given the stark dissimilarity of the cornea from the RPE and choroid, both in form and function, the robust behavior of VEGF-A in both models of inflammatory neovascularization indicates the fundamental importance of context in determining its role in wound healing.

Example 13

Methods

Animals. Male wild-type C57BL/6 mice and SHP-1$^{-/-}$ mice were purchased from Jackson Laboratories, and Ccl2$^{-/-}$, Ccr2$^{-/-}$, Ccl3$^{-/-}$, and Ccr5$^{-/-}$ strains, generated as described previously (Lu, B. et al. *Abnormalities in monocyte recruitment and cytokine expression in monocyte chemoattractant protein 1-deficient mice*. (1998) J Exp Med 187, 601-8; Kuziel, W. A. et al. *Severe reduction in leukocyte adhesion and monocyte extravasation in mice deficient in CC chemokine receptor 2*. (1997) Proc Natl Acad Sci USA 94, 12053-8; Cook, D. N. et al. *Requirement of MIP-1α for an inflammatory response to viral infection*. (1995) Science 269, 1583-5; Huffnagle, G. B. et al. *Cutting edge: Role of C-C chemokine receptor 5 in organ-specific and innate immunity to Cryptococcus neoformans*. (1999) J Immunol 163, 4642-6; Kuziel, W. A. et al. *CCR5 deficiency is not protective in the early stages of atherogenesis in apoE knockout mice*. (2003) Atherosclerosis 167, 25-32) and backcrossed at least 8 to 10 times to C57BL/6, and Sparc$^{-/-}$ and Sparc$^{+/+}$ strains on a mixed C57BL6×129/SvJ background (Norose, K. et al. *SPARC deficiency leads to early-onset cataractogenesis. Invest*. (1998) Ophthalmol. Vis. Sci. 39, 2674-2680) were anesthetized by intramuscular injection of ketamine (50 mg/kg) and xylazine (10 mg/kg), and pupils were dilated with topical 1% tropicamide (Alcon). All mice were 6-8 weeks of age. Experiments were approved by the University of Kentucky Institutional Animal Care and Use Committee.

CNV. Laser photocoagulation (532 nm, 200 mW, 100 ms, 75 μm) (OcuLight GL, Iridex) was performed on both eyes of each animal to induce CNV as described. See Sakurai, E. et al. *Targeted disruption of the CD18 or ICAM-1 gene inhibits choroidal neovascularization*. (2003) Invest Ophthalmol Vis Sci 44, 2743-9; and Sakurai, E., Anand, A., Ambati, B. K., van Rooijen, N. & Ambati, J. *Macrophage depletion inhibits experimental choroidal neovascularization*. (2003) Invest Ophthalmol Vis Sci 44, 3578-85. CNV volumes were measured by scanning laser confocal microscope (TCS SP, Leica) as reported with 0.5% FITC-conjugated *Griffonia simplicifolia* Isolectin B4 (Vector Laboratories) or 0.5% FITC-conjugated rat anti-mouse PECAM-1 (BD Pharmingen). Volumes obtained by lectin and CD31 staining were highly correlated ($r^2$=0.95).

Drug treatments. VEGF-A$_{164}$ (4-12 ng), VEGF-A$_{120}$ (2.7-27 ng), PLGF-1 (12.5-1,250 ng), mouse PLGF-2 (165-1,650 ng), mouse Ccl-2 (0.55 ng), neutralizing goat antibodies to mouse VEGF-A (5-20 ng), mouse VEGFR-1 (6-18 μg), mouse VEGFR-2 (25-250 ng), or rat NP-1 (200-500 ng; all R&D Systems), recombinant human SPARC (100-300 ng; purified in the laboratory of E. H. Sage) or neutralizing mouse antibody to human SPARC (4-12 μg; purified in the laboratory R. W. Brekken, University of Texas), neutralizing rabbit antibody to rat NP-2 (200-500 ng; gifts of D. D. Ginty, Johns Hopkins University and S. Niclou, Netherlands Institute for Brain Research (Shearer, M. C. et al. *The astrocyte/meningeal cell interface is a barrier to neurite outgrowth which can be overcome by manipulation of inhibitory molecules or axonal signalling pathways*. (2003) Mol Cell Neurosci 24, 913-25)), VEGF-E (4-12 ng; Cell Sciences), FGF-2 (1.5-5 ng; Intergen), CoCl$_2$ (0.1 μg), H$_2$O$_2$ (0.1 μg; both Sigma-Aldrich), BMOV (50 μg; gift of J. H. MacNeill & C. Orvig, University of British Columbia), dissolved in phosphate buffered saline (PBS; Sigma-Aldrich), or SU5416 (0.3 ng), SU1498 (3.5 ng), AG1295 (15 ng), SSG (125 ng), calpeptin (1.25 μg; all Calbiochem) or DBAPBA (1.25 μg; gift of H. Nakamura, Gakushuin University), dissolved in dimethyl sulfoxide (Sigma-Aldrich), were injected into the mouse vitreous cavity in a total volume of 1 μl. ZnPP or CuPP (25 mg/kg; Frontier Scientific), or L-NAME or D-NAME (10 mg/kg; Sigma-Aldrich) were injected via tail vein (12 h before and immediately after laser injury). Clodronate or PBS liposomes (Roche Diagnostics GmbH) were injected (200 μl) via tail vein and into the subconjunctival space (10 μl), 2 days before and immediately after laser injury. Rat antibody to mouse Gr-1 antibody (eBioscience) or rat IgG (Sigma-Aldrich) was injected (7.5 μg) intraperitoneally 24 h before and immediately after laser injury. Antibody to NK1.1, antibody to CD4; antibody to CD8 antibodies were injected (200 μg) intraperioneally 48 hours before and immediately after laser injury.

Western blotting. Equal amounts of total protein from RPE/choroid were resolved in SDS 4-20% polyacrylamide gradient gel and transferred to nitrocellulose membranes for western blotting with rabbit antibody to rat HO-1 (1:5,000; StressGen), goat antibody to mouse VEGFR-1 (1:500; R&D Systems), rabbit antibody to mouse VEGFR-2 (1:1,000; Upstate), rabbit antibody to human SPARC (1:500; R&D Systems), rat antibody to mouse PEDF (1:400; R&D Systems), rabbit antibody to mouse p21$^{Cip1/WAF1}$ (1:500; Santa Cruz), rabbit antibody to human p27$^{Kip1}$ (1:500; Santa Cruz), and of rabbit antibody to human cyclin D1 (1:500; Santa Cruz). Equal loading was assessed by blotting with rabbit antibody to human GAPDH (1:2,000; Abcam).

Immunoprecipitation and immunoblotting. RPE/choroid lysates were immunoprecipitated with goat antibody to mouse VEGFR-1 or rabbit antibody to mouse VEGFR-2 immobilized to protein G-agarose, subjected to SDS-PAGE, immunoblotted with mouse monoclonal antibody to phosphotyrosine (1:1,000; Upstate), rabbit antibody to human SHP-1 (1:1,000; Santa Cruz), rabbit antibody to human PTP-1B (1:1,000; Santa Cruz), or rabbit antibody to HCPTPA (1:10,000; gift. of M. C. Lecomte, INSERM) and subsequently reprobed with rat antibodies to mouse VEGFR-1 or VEGFR-2 (both 1:500; R&D Systems).

Flow cytometry. Single cell suspensions isolated from mouse RPE/choroids via collagenase D (20 U/ml; Roche Diagnostics) treatment were incubated in Fc block (0.5 mg/ml; BD Pharmingen) for 15 min on ice. Rabbit antibody to mouse VEGFR-1 (1:250; Santa Cruz) coupled with Cy5-donkey antibody to rabbit IgG Ab (1:250) and Phycoerythrin-conjugated rat antibody to mouse VEGFR-2 (1:250; eBioscience) were used to quantitate cell surface receptor expression. Macrophages defined as F4/80$^+$CD11c$^-$ cells, were gated by rat antibody to mouse Cy5-F4/80 (1:30; Serotec) and hamster antibody to mouse FITC-CD11c (1:100; Serotec), CEC by FITC-conjugated rat antibody to mouse CD31 (1:250; BD Biosciences), and RPE cells by FITC-conjugated mouse antibody to human pan-cytokeratin (1:250; Sigma-Aldrich) staining following fixation with 4% paraformaldehyde and permeabilization with 1% Triton X-100 (Sigma Aldrich) and subjected to FACS analysis (FACSCalibur, BD Biosciences). DNA content was analyzed following incubation with propidium iodide (0.05 mg/ml; Molecular Probes) containing 0.1% Triton X-100 and RNase A (0.1 mg/ml; Roche).

Corneal neovascularization. Neovascularization of the cornea following chemical and mechanical injury was measured as reported previously. Ambati, B. K. Et al. *Sustained inhibition of corneal neovascularization by genetic ablation of*

CCR5. (2003) Invest Ophthalmol Vis Sci 44, 590-3. Ambati, B. K., Joussen, A. M., Kuziel, W. A., Adamis, A. P. & Ambati, J. *Inhibition of corneal neovascularization by genetic ablation of CCR2.* (2003) Cornea 22, 465-7. Vascular endothelium was stained with FITC-conjugated rat antibody to CD31 (1:333; BD Pharmingen) and rabbit antibody to mouse LYVE-1 (1:200; Abcam), followed by Cy3-conjugated goat anti-rabbit IgG (1:100; Jackson Immunoresearch).

Mononuclear cell isolation and FACS analysis. At each time point, blood was obtained from the heart immediately before sacrifice and separated by Histopaque-1083 (Sigma) density gradient centrifugation. Light density mononuclear cells were harvested, washed twice with Dulbecco's phosphate-buffered saline (PBS; no calcium or magnesium) (Fisher) supplemented with 2 mM EDTA (DPBS-E). Contaminated red blood cells were hemolyzed using ammonium chloride solution (Stem Cell Technologies).

ELISA. VEGF-A, Ccl-2, and Ccl-3 levels in the RPE and choroid in vivo or in cell culture supernatants were measured by ELISA (R&D Systems) and normalized to total protein concentration (Biorad).

Statistics. CNV volumes were compared using a hierarchical logistic regression using repeated measures analysis as described. See Sakurai, E. et al. *Targeted disruption of the CD18 or ICAM-1 gene inhibits choroidal neovascularization.* (2003) Invest Ophthalmol Vis Sci 44, 2743-9. Sakurai, E., Anand, A., Ambati, B. K., van Rooijen, N. & Ambati, J. *Macrophage depletion inhibits experimental choroidal neovascularization.* (2003) Invest Ophthalmol Vis Sci 44, 3578-85. Other data were analyzed by ANOVA using Fisher's protected least significant difference test for multiple comparisons or unpaired two-tailed t-test. Results are expressed as mean±s.e.m (n refers to number of animals for in vivo experiments). Type-I error not exceeding 0.05 was deemed significant.

Although illustrative embodiments of the present invention have been described in detail, it is to be understood that the present invention is not limited to those precise embodiments, and that various changes and modifications can be effected therein by one skilled in the art without departing from the scope and spirit of the invention as defined by the appended claims.

What is claimed:

1. An ophthalmic composition for treatment of ocular neovascularization comprising an effective amount of a SPARC antagonist, a compound selected from VEGF-A, PLGF-1 and PLGF-2, and a pharmaceutically acceptable carrier suitable for injection into the eye or topical application to the eye, wherein said composition inhibits ocular neovascularization.

2. The composition of claim 1 wherein the SPARC antagonist is an antibody to SPARC or antibody fragment that binds to SPARC.

3. The composition of claim 1 wherein the SPARC antagonist is siRNA that binds to and inhibits expression of the SPARC gene.

4. The composition of claim 1 wherein the SPARC antagonist is a peptide that binds to and inhibits the active site of SPARC.

* * * * *